(12) United States Patent
Badorc et al.

(10) Patent No.: US 7,442,708 B2
(45) Date of Patent: Oct. 28, 2008

(54) 1,2,3-SUBSTITUTED INDOLIZINE DERIVATIVES, INHIBITORS OF FGFS, METHOD FOR MAKING SAME AND PHARMACEUTICAL COMPOSITIONS CONTAINING SAME

(75) Inventors: Alain Badorc, Roquettes (FR); Francoise Bono, Toulouse (FR); Marie-Francoise Bordes, Labarthe sur Leze (FR); Nathalie Guillo, Toulouse (FR); Jean-Marc Herbert, Tournefeuille (FR)

(73) Assignee: Sanofi-Aventis, Paris (FR)

( * ) Notice: Subject to any disclaimer, the term of this patent is extended or adjusted under 35 U.S.C. 154(b) by 389 days.

(21) Appl. No.: 10/509,919

(22) PCT Filed: Apr. 2, 2003

(86) PCT No.: PCT/FR03/01030
§ 371 (c)(1),
(2), (4) Date: Oct. 4, 2004

(87) PCT Pub. No.: WO03/084956
PCT Pub. Date: Oct. 16, 2003

(65) Prior Publication Data
US 2005/0203126 A1 Sep. 15, 2005

(30) Foreign Application Priority Data
Apr. 4, 2002 (FR) .................... 02 04220

(51) Int. Cl.
*A01N 43/42* (2006.01)
*A61K 31/44* (2006.01)
*C07D 221/02* (2006.01)
(52) U.S. Cl. ...................... 514/299; 546/112
(58) Field of Classification Search ............... 546/112; 514/299
See application file for complete search history.

(56) References Cited

U.S. PATENT DOCUMENTS

| | | | |
|---|---|---|---|
| 4,378,362 A | 3/1983 | Rosseels | |
| 4,400,387 A | 8/1983 | Rosseels | |
| 4,499,095 A | 2/1985 | Russels et al. | |
| 4,957,925 A | 9/1990 | Gubin et al. | |
| 7,078,209 B2 | 7/2006 | Ledford et al. | |
| 2006/0199962 A1* | 9/2006 | Alcouffe et al. | 546/138 |

FOREIGN PATENT DOCUMENTS

| | | |
|---|---|---|
| EP | 0 097 636 A | 1/1984 |
| EP | 0 235 111 A | 9/1987 |
| WO | WO 00 71129 A | 11/2000 |
| WO | WO 00/71129 A1 | 11/2000 |

OTHER PUBLICATIONS

Zhang et al., Synthesis, "A one-step approach to 1-(fluoroalkyl)indolizine derivatives", 1999, vol. 1, pp. 51-54.*
Bora et al., Organic Letters, 2003, vol. 5, pp. 435-438.*
Kakehi et al., Bulletin of the chemical society of Japan, 1996, vol. 69, pp. 1769-1776.*
Wei et al., Journal of the chemical society, Perkin Transactions 1: Organic and Bio-organic chemistry, 1993, vol. 20, pp. 2487-2489.*
Tamura et al., Journal of the chemical society, Perkin Transactions 1: Organic and Bio-organic chemistry, 1973, vol. 19, pp. 2091-2095.*
Overzet et al., Journal of pharmaceutical and biomedical analysis, 1984, vol. 2, pp. 3-17.*
Rosseels, et al., Study in the Indolizines Series. V. Effect of Indolizine Substitution i Position 1 in the Butoprozine Series, European J. of Med. Chemistry; 1983; 18(4); pp. 339-346.
*Compounds for Screening*, SPECS and bioSPECS XP002224380, Database Chemcats chemical abstracts service, Columbus, Ohio; Jul. 1, 2001.

* cited by examiner

*Primary Examiner*—D. Margaret Seaman
*Assistant Examiner*—Niloofar Rahmani
(74) *Attorney, Agent, or Firm*—Paul R. Darkes; Paul E. Dupont

(57) ABSTRACT

Compounds of formula I or salts thereof:

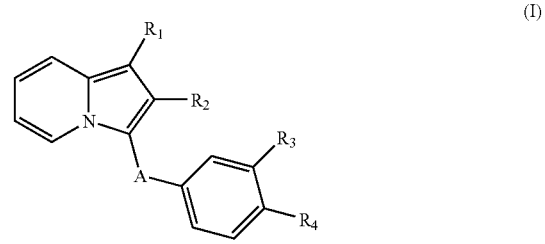

(I)

Figure 1:
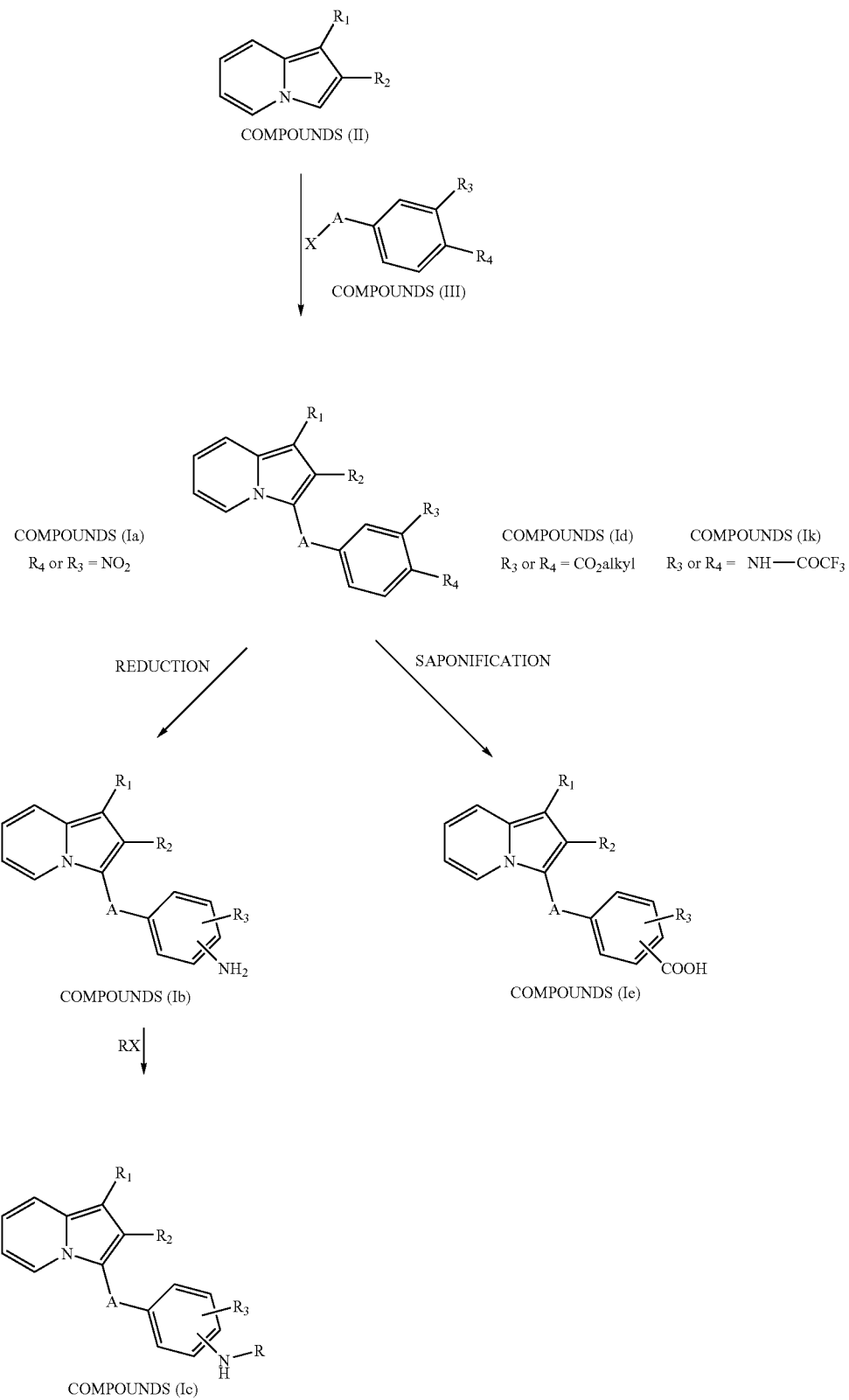

in which
$R_1$ represents —OH, $(C_1$-$C_5)$alkoxy, carboxyl, $(C_2$-$C_6)$ alkoxycarbonyl, —$NR_5R_6$, —NH—$SO_2$-Alk, —NH—$SO_2$-Ph, —NH—CO-Ph, —N(Alk)-CO-Ph, —NH—CO—NH-Ph, —NH—CO-Alk, —NH—$CO_2$-Alk, —O—$(CH_2)_n$-cAlk, —O-Alk-$COOR_7$, —O-Alk-O—$R_8$, —O-Alk-OH, —O-Alk-$C(NH_2)$:NOH, —O-Alk-$NR_5R_6$, —O-Alk-CN, —O—$(CH_2)_n$-Ph, —O-Alk-CO—$NR_5R_6$, —CO—NH—$(CH_2)_m$—$COOR_7$, —CO—NH-Alk
$R_2$ represents H, $(C_1$-$C_5)$alkyl, $(C_1$-$C_5)$alkyl halide, $(C_3$-$C_6)$ cycloalkyl or phenyl which is optionally substituted,
A represents —CO—, —SO— or —$SO_2$—,
$R_3$ and $R_4$ which are identical or different, each represent H, $(C_1$-$C_5)$alkoxy, amino, carboxyl, $(C_2$-$C_6)$alkoxycarbonyl, —OH, nitro, hydroxyamino, -Alk-$COOR_7$, —$NR_5R_6$, —NH-Alk-$COOR_7$, —NH—COO-Alk, —$N(R_{11})$—$SO_2$-Alk-$NR_9R_{10}$, —$N(R_{11})$—$SO_2$-Alk, —$N(R_{11})$-Alk-$NR_5R_6$, —$N(R_{11})$—CO-Alk-$NR_9R_{10}$, —$N(R_{11})$—CO-Alk, —$N(R_{11})$—CO—$CF_3$, —NH-Alk-HetN, —O-Alk-$NR_9R_{10}$, —O-Alk-CO—$NR_5R_6$, —O-Alk-HetN, or $R_3$ and $R_4$ form together a 5- to 6-membered unsaturated heterocycle, are inhibitors of basic fibroblast growth factors.

7 Claims, No Drawings

1,2,3-SUBSTITUTED INDOLIZINE DERIVATIVES, INHIBITORS OF FGFS, METHOD FOR MAKING SAME AND PHARMACEUTICAL COMPOSITIONS CONTAINING SAME

The subject of the present invention is novel 1,2,3-substituted indolizine derivatives, which are inhibitors of FGFs (basic fibroblast growth factors), the method for preparing them and the pharmaceutical compositions containing them.

FGFs are a family of polypeptides which are synthesized by a large number of cells during embryonic development and by cells of adult tissues under various pathological conditions.

Some derivative of naphthyridinediamines and corresponding ureas are known which are selective inhibitors of FGF-1 (Batley B. et al., *Life Sciences*, (1998), Vol. 62 No. 2, pp. 143-150; Thompson A. et al., *J. Med. Chem.*, (2000), Vol. 43, pp. 4200-4211).

Some indolizine derivatives are described in patent applications and patents U.S. Pat. No. 4,378,362, FR 2 341 578, GB 2 064 536, EP 0 097 636, EP 302 792, EP 0 382 628, and EP 0 235 111. These compounds are useful in the treatment of angina pectoris and arrhythmia. Calcium translocation inhibiting properties are described for some of these compounds.

Patent Application EP 0 022 762 also describes some indolizine derivatives which possess a xanthine oxidase and adenosine deaminase inhibiting activity and a uricosuric activity. These compounds may be used in the treatment of physiological disorders which occur following an excess of uric acid, disruptions of the immune system and as parasitic agents.

It has now been found that some compounds, derived from indolizine, are potent antagonists of the binding of FGFs to its receptors.

Accordingly, the subject of the present invention is novel indolizine derivatives of formula I.

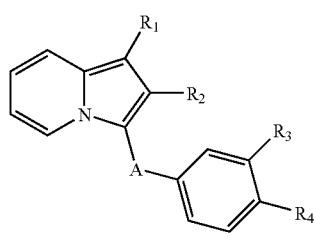

(I)

in which
R$_1$ represents a hydroxyl radical, a linear or branched alkoxy radical of 1 to 5 carbon atoms, a carboxyl radical, an alkoxycarbonyl radical of 2 to 6 carbon atoms or a radical of formula:
—NR$_5$R$_6$
—NH—SO$_2$-Alk
—NH—SO$_2$-Ph
—NH—CO-Ph
—N(Alk)-CO-Ph
—NH—CO—NH-Ph
—NH—CO-Alk
—NH—CO$_2$-Alk
—O—(CH$_2$)$_n$-cAlk
—O-Alk-COOR$_7$
—O-Alk-O—R$_8$
—O-Alk-OH
—O-Alk-C(NH$_2$):NOH
—O-Alk-NR$_5$R$_6$
—O-Alk-CN
—O—(CH$_2$)$_n$-Ph
—O-Alk-CO—NR$_5$R$_6$
—CO—NH—(CH$_2$)m-COOR$_7$
—CO—NH-Alk
in which
Alk represents an alkyl radical or a linear or branched alkylene radical of 1 to 5 carbon atoms,
cAlk represents a cycloalkyl radical of 3 to 6 carbon atoms,
n represents an integer from 0 to 5,
m represents an integer from 1 to 5,
R$_5$ and R$_6$, which are identical or different, each represent a hydrogen atom, a linear or branched alkyl radical of 1 to 5 carbon atoms or a benzyl radical,
R$_7$ represents a hydrogen atom or an alkyl radical of 1 to 5 carbon atoms,
R$_8$ represents an alkyl radical of 1 to 5 carbon atoms or a radical —CO-Alk,
Ph represents a phenyl radical which is optionally substituted with one or more halogen atoms, with one or more alkoxy radicals of 1 to 5 carbon atoms, with one or more carboxyl radicals or with one or more alkoxycarbonyl radicals of 2 to 6 carbon atoms,
R$_2$ represents a hydrogen atom, an alkyl radical of 1 to 5 carbon atoms, an alkyl halide radical of 1 to 5 carbon atoms containing 3 to 5 halogen atoms, a cycloalkyl radical of 3 to 6 carbon atoms or a phenyl radical which is optionally substituted with one or more halogen atoms, with one or more alkoxy radicals of 1 to 5 carbon atoms, with one or more carboxyl radicals or with one or more alkoxycarbonyl radicals of 2 to 6 carbon atoms,
A represents a radical —CO—, —SO— or —SO$_2$—,
R$_3$ and R$_4$, which are identical or different, each represent a hydrogen atom, an alkoxy radical of 1 to 5 carbon atoms, an amino radical, a carboxyl radical, an alkoxycarbonyl radical of 2 to 6 carbon atoms, a hydroxyl radical, a nitro radical, a hydroxyamino radical, a radical of formula
-Alk-COOR$_7$
—NR$_5$R$_6$
—NH-Alk-COOR$_7$
—NH—COO-Alk
—N(R$_{11}$)—SO$_2$-Alk-NR$_9$R$_{10}$
—N(R$_{11}$)—SO$_2$-Alk
—N(R$_{11}$)-Alk-NR$_5$R$_6$
—N(R$_{11}$)—CO-Alk-NR$_9$R$_{10}$
—N(R$_{11}$)—CO-Alk
—N(R$_{11}$)—CO—CF$_3$
—NH-Alk-HetN
—O-Alk-NR$_9$R$_{10}$
—O-Alk-CO—NR$_5$R$_6$
—O-Alk-HetN
in which n, m, Alk, R$_5$, R$_6$ and R$_7$ have the meaning given above for R$_1$, and
R$_9$ and R$_{10}$ which are identical or different, each represent a hydrogen atom or an alkyl radical of 1 to 5 carbon atoms,
R$_{11}$ represents a hydrogen atom or a radical -Alk-COOR$_{12}$ where R$_{12}$ represents a hydrogen atom, an alkyl radical of 1 to 5 carbon atoms or a benzyl radical, HetN represents a 5- or 6-membered heterocycle containing at least one nitrogen atom and optionally another heteroatom chosen from nitrogen and oxygen, or $R_3$ and $R_4$ form together a 5- to 6-membered unsaturated heterocycle, provided, however, that when $R_3$ represents an alkoxy radical and $R_4$ represents a radical —O-Alk-$NR_9R_{10}$ or a hydroxyl radical, $R_1$ does not represent an alkoxy radical, optionally in the form of one of their pharmaceutically acceptable salts.

A compound of formula I is preferred in which $R_1$ represents a hydroxyl radical, a linear or branched alkoxy radical of 1 to 5 carbon atoms, a carboxyl radical, an alkoxycarbonyl radical of 2 to 6 carbon atoms or a radical of formula:
—$NR_5R_6$
—NH—$SO_2$-Alk
—NH—$SO_2$-Ph
—NH—CO-Ph
—N(Alk)-CO-Ph
—NH—CO—NH-Ph
—NH—CO-Alk
—NH—$CO_2$-Alk
—O—$(CH_2)_n$-cAlk
—O-Alk-$COOR_7$
—O-Alk-O—$R_8$
—O-Alk-OH
—O-Alk-$NR_5R_6$
—O-Alk-CN
—O—$(CH_2)_n$-Ph
—O-Alk-CO—$NR_5R_6$
—CO—NH—$(CH_2)_m$—$COOR_7$
—CO—NH-Alk in which
Alk represents an alkyl radical or a linear or branched alkylene radical of 1 to 5 carbon atoms,
cAlk represents a cycloalkyl radical of 3 to 6 carbon atoms,
n represents an integer from 0 to 5,
m represents an integer from 1 to 5,
$R_5$ and $R_6$, which are identical or different, each represent a hydrogen atom, a linear or branched alkyl radical of 1 to 5 carbon atoms or a benzyl radical,
$R_7$ represents a hydrogen atom or an alkyl radical of 1 to 5 carbon atoms,
$R_8$ represents an alkyl radical of 1 to 5 carbon atoms or a radical —CO-Alk,
Ph represents a phenyl radical which is optionally substituted with one or more halogen atoms, with one or more alkoxy radicals of 1 to 5 carbon atoms, with one or more carboxyl radicals or with one or more alkoxycarbonyl radicals of 2 to 6 carbon atoms,
$R_2$ represents an alkyl radical of 1 to 5 carbon atoms, a trifluoromethyl radical, a cycloalkyl radical of 3 to 6 carbon atoms or a phenyl radical which is optionally substituted with one or more halogen atoms, with one or more alkoxy radicals of 1 to 5 carbon atoms, with one or more carboxyl radicals or with one or more alkoxycarbonyl radicals of 2 to 6 carbon atoms,
A represents a radical —CO— or —$SO_2$—,
$R_3$ and $R_4$, which are identical or different each represent a hydrogen atom, an alkoxy radical of 1 to 5 carbon atoms, an amino radical, a carboxyl radical, an alkoxycarbonyl radical of 2 to 6 carbon atoms, a nitro radical, a hydroxyamino radical, a radical of formula
-Alk-$COOR_7$
—$NR_5R_6$
—NH-Alk-$COOR_7$
—NH—COO-Alk
—N($R_{11}$)—$SO_2$-Alk-$NR_9R_{10}$
—N($R_{11}$)—$SO_2$-Alk
—N($R_{11}$)-Alk-$NR_5R_6$
—N($R_{11}$)—CO-Alk-$NR_9R_{10}$
—N($R_{11}$)—CO-Alk
—N($R_{11}$)—CO—$CF_3$
—NH-Alk-HetN in which n, m, Alk, $R_5$, $R_6$ and $R_7$ have the meaning given above for $R_1$, and
$R_9$ and $R_{10}$, which are identical or different, each represent a hydrogen atom or an alkyl radical of 1 to 5 carbon atoms,
$R_{11}$ represents a hydrogen atom or a radical -Alk-$COOR_{12}$ where $R_{12}$ represents a hydrogen atom, an alkyl radical of 1 to 5 carbon atoms or a benzyl radical,
HetN represents a 5- or 6-membered heterocycle containing at least one nitrogen atom and optionally another heteroatom chosen from nitrogen and oxygen, optionally in the form of one of their pharmaceutically acceptable salts.

A compound of formula I is particularly preferred in which
$R_1$ represents an alkoxy radical of 1 to 5 carbon atoms, a carboxyl radical, a radical —O-Alk-COOH in which Alk represents a linear or branched alkylene radical of 1 to 5 carbon atoms, a radical of formula —O-Alk-Ph in which Alk represents an alkylene radical of 1 to 5 carbon atoms and Ph represents a phenyl radical which is optionally substituted with one or more halogen atoms or with one or more alkoxy radicals of 1 to 5 carbon atoms or with one or more carboxyl radicals, a radical of formula —NH—CO-Ph, a radical of formula —NH—$SO_2$-Ph or a radical of formula —NH—CO—NH-Ph,
$R_2$ represents an alkyl radical of 1 to 5 carbon atoms,
A represents a radical —CO—,
$R_3$ and $R_4$, which are different, each represent a hydrogen atom, an alkoxy radical of 1 to 5 carbon atoms, an amino radical, a carboxyl radical or an alkoxycarbonyl radical of 2 to 6 carbon atoms, optionally in the form of one of its pharmaceutically acceptable salts.

Among the compounds of the invention, the compounds which are particularly preferred are the following:
(4-amino-3-methoxyphenyl)(1-methoxy-2-methylindolizin-3-yl)methanone
3-(4-amino-3-methoxybenzoyl)-2-methylindolizin-1-yl carboxylic acid
2-{[3-(4-amino-3-methoxybenzoyl)-2-methylindolizin-1-yl]oxy}acetic acid
(4-amino-3-methoxyphenyl){1-[(4-chlorobenzyl)-oxy]-2-methylindolizin-3-yl}methanone
(4-amino-3-methoxyphenyl){1-[(3-methoxybenzyl)oxy]-2-methylindolizin-3-yl}methanone
4-({[3-(4-amino-3-methoxybenzoyl)-2-methylindolizin-1-yl]oxy}methyl)benzoic acid
3-(4-carboxybenzoyl)-2-methylindolizin-1-yl carboxylic acid
methyl 3-[(1-methoxy-2-methylindolizin-3-ylcarbonyl]benzoate
4-[(1-methoxy-2-methylindolizin-3-yl)carbonyl]benzoic acid
2-amino-5-[(1-methoxy-2-methylindolizin-3-yl)carbonyl]benzoic acid 2-amino-5-({1-[(3-methoxybenzoyl)amino]-2-methylindolizin-3-yl}carbonyl)benzoic acid 2-amino-5-({2-methyl-1-[(3,4,5-trimethoxybenzoyl)amino]indolizin-3-yl}carbonyl)benzoic acid 2-amino-5-({1-{[(3-methoxyphenyl)sulphonyl]amino}-2-methylindolizin-3-yl}carbonyl)benzoic acid optionally in the form of one of its pharmaceutically acceptable salts.

The present invention also relates to a method for preparing the compounds of formula I, characterized in that A) an indolizine derivative of formula II,

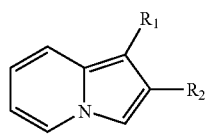
(II)

in which $R_1$ and $R_2$ have the meaning given for formula I, but $R_2$ does not represent a hydrogen atom or an alkyl halide radical, is condensed with a derivative of formula III,

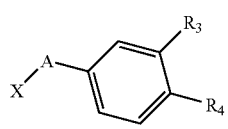
(III)

in which X represents a halogen atom and $R_3$ or $R_4$, which are identical or different, each represent a hydrogen atom, a nitro radical, a trifluoroacetamido radical or an alkoxycarbonyl radical of 2 to 6 carbon atoms, in order to obtain the compounds of formula Ia, Id or Ik,

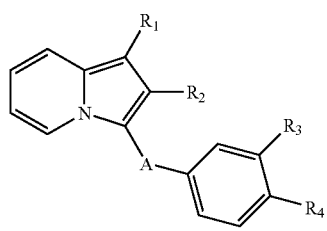
(Ia)

$R_3$ and/or $R_4$ = —NO$_2$

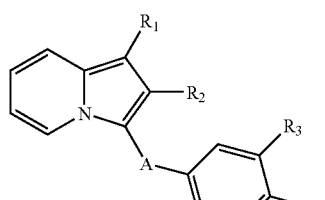
(Id)

$R_3$ and/or $R_4$ = —CO$_2$Alkyl

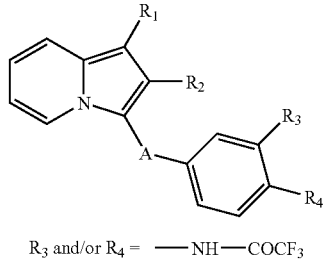
(Ik)

$R_3$ and/or $R_4$ = —NH—COCF$_3$ and then, a) the compounds of formula Ia are subjected to a reduction in order to obtain the compounds of formula Ib,

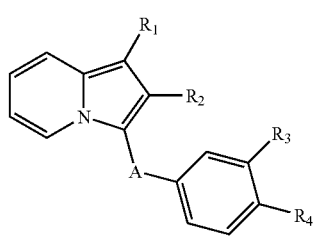
(Ib)

$R_3$ and/or $R_4$ = —NH$_2$ in which $R_3$ and/or $R_4$ represent an amino radical, which compounds of formula Ib then are subjected to the action of an alkyl halide in order to obtain the compounds of formula I for which $R_4$ and/or $R_3$ represent a radical —NR$_5$R$_6$ (in which $R_5$ represents a hydrogen atom and $R_6$ represents an alkyl radical of 1 to 5 carbon atoms) and a radical —NH-Alk-NR$_5$R$_6$ or a radical —NH-Alk-COOR$_7$ (in which $R_7$ does not represent a hydrogen atom) from which, by a subsequent saponification, the compounds of formula I are obtained for which $R_4$ and/or $R_3$ represent a radical —NH-Alk-COOR$_7$ in which $R_7$ represents a hydrogen atom, or are subjected to acylation in order to obtain the compounds of formula I for which $R_4$ and/or $R_3$ represent a radical —NH—CO-Alk, or a radical —NH—CO-Alk-NR$_9$R$_{10}$, which are then subjected to alkylation in order to obtain a radical —N(R$_{11}$)—CO-Alk or a radical —N(R$_{11}$)—CO-Alk-NR$_9$R$_{10}$ where R$_{11}$ represents a radical -Alk-COOR$_{12}$ in which R$_{12}$ does not represent a hydrogen atom, the latter compounds are then optionally subjected to saponification in order to obtain the compounds of formula I for which $R_4$ and/or $R_3$ represent a radical —N(R$_{11}$)—CO-Alk or a radical —N(R$_{11}$)—CO-Alk-NR$_9$R$_{10}$ where R$_1$, represents a radical -Alk-COOH, or are subjected to sulphonylation in order to obtain the compounds of formula I for which $R_4$ and/or $R_3$ represent a radical —NH—SO$_2$-Alk or a radical —NH—SO$_2$-Alk-NR$_9$R$_{10}$, which are then subjected to alkylation in order to obtain a radical —N(R$_{11}$)—SO$_2$-Alk or a radical —N(R$_{11}$)—SO$_2$-Alk-NR$_9$R$_{10}$ where R$_{11}$ represents a radical -Alk-COOR$_{12}$ in which R$_{12}$ does not represent a hydrogen atom, the latter compounds are then optionally subjected to saponification in order to obtain the compounds of formula I for which $R_4$ and/or $R_3$ represent a radical —N($R_{11}$)—SO$_2$-Alk or a radical —N($R_{11}$)—SO$_2$-Alk-NR$_9$R$_{10}$ where $R_{11}$ represents a radical -Alk-COOH b) the compounds of formula Id in which $R_3$ and/or $R_4$ represent an alkoxycarbonyl radical are subjected to saponification in order to obtain the compounds of formula I in which $R_3$ and/or $R_4$ represent a carboxyl radical, or c) when $R_1$ represents a benzyloxy radical, the compounds of formula Ia are subjected to the action of trifluoroacetic acid or the compounds of formula Id to hydrogenation, in order to obtain the compounds of formula If,

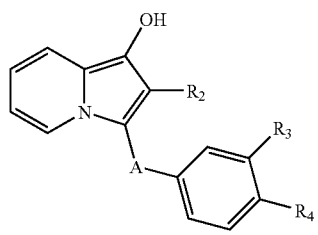
(If)

in which $R_3$ and/or $R_4$ have the meanings given above, and then the compounds of formula If are subjected to O-alkylation in order to obtain the compounds of formula Ig,

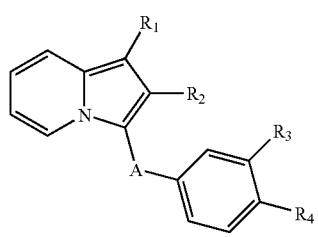
(Ig)

in which $R_3$ and/or $R_4$ have the meanings given above, and $R_1$ represents a linear or branched alkoxy radical of 1 to 5 carbon atoms, a radical —O—(CH$_2$)$_n$-cAlk, a radical —O-Alk-COOR$_7$, a radical —O-Alk-NR$_5$R$_6$, a radical —O—(CH$_2$)$_n$—Ph, or a radical —O-Alk-O—R$_8$—which, when R$_8$ represents a radical —COCH$_3$, can give, by subsequent saponification, a radical —O-Alk-OH—or a radical —O-Alk-CN which, by treatment with hydroxylamine, gives a radical —O-Alk-C(NH$_2$)=NOH, or d) when $R_1$ represents an alkoxycarbonyl radical, the compounds of formula Ia are subjected to saponification in order to obtain the compounds of formula Ih,

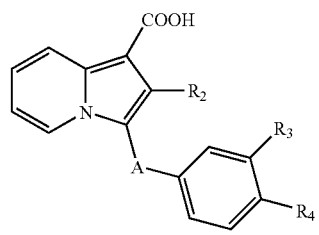
(Ih)

in which $R_3$ and/or $R_4$ have the meanings given above, which are then subjected to the action of an amine derivative in order to obtain the compounds of formula I in which $R_1$ represents a radical —CO—NH-Alk, or to the action of an amino acid derivative in order to obtain the compounds of formula I in which $R_1$ represents a radical —CO—NH—(CH$_2$)$_m$-COOR$_7$ or e) when $R_1$ represents a radical —NH—CO$_2$tButyl, the compounds of formula Ia or Id are subjected
either to alkylation followed by deprotection and an optional second alkylation in order to obtain the compounds of formula Ii,
or to deprotection, followed by acylation in order to obtain the compounds of formula Ij in which $R_5$ represents a hydrogen atom, followed by an optional alkylation in order to obtain the compounds of formula Ij in which $R_5$ represents an alkyl radical

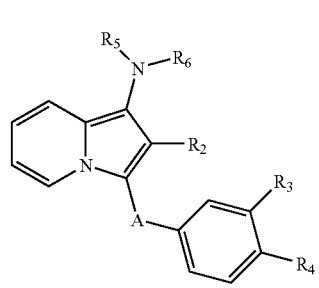
(Ii)

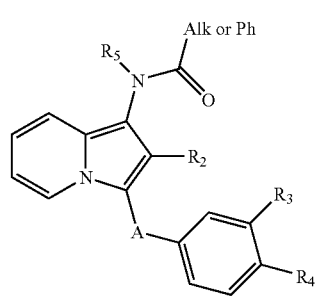
(Ij)

f) when $R_1$ represents a radical —NH—CO$_2$tButyl, the compounds of formula Ik are subjected either to deprotection, followed by acylation in order to obtain the compounds of formula II

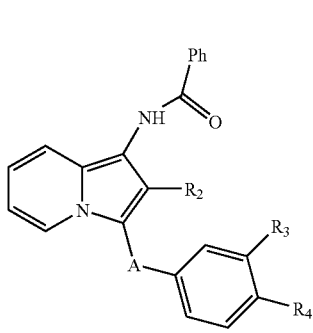

(II)

or to deprotection followed by sulphonylation in order to obtain the compounds of formula Im

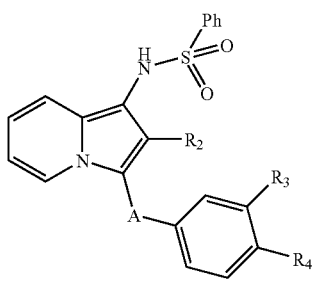

(Im)

or to deprotection, followed by a treatment with a phenyl isocyanate in order to obtain the compounds of formula In

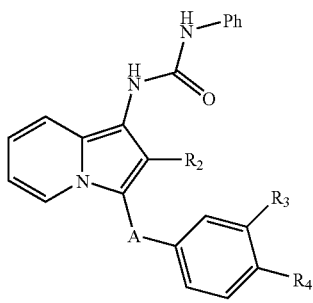

(In)

OR

B) when $R_1$ represents an electron-attracting group, $R_2$ represents a hydrogen atom or an alkyl halide radical and A represents a radical —CO—, pyridine is reacted with a bromoacetophenone of formula IV,

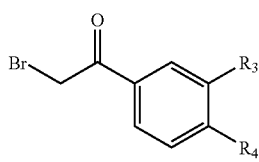

(IV)

in order to obtain the compounds of formula V,

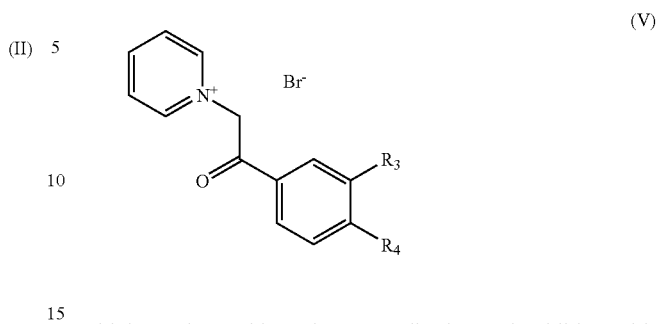

(V)

which are then subjected to a 1,3-dipolar cycloaddition with ethyl acrylate or a halogenated derivative of ethyl crotonate in the presence of an oxidizing agent in order to obtain the compounds of formula Ia in which $R_1$ represents an ethoxycarbonyl radical and $R_2$ represents a hydrogen atom or an alkyl halide radical.

FIGS. 1 and 2 give the diagram for the synthesis of products Ia to Ig and Ik.

The compounds of formula Ia, in which $R_2$ represents a hydrogen atom or an alkyl halide radical, A represents a radical —CO— and $R_1$ is an electron-attracting group such as alkoxycarbonyl, are prepared according to known cycloaddition methods [*J. Heterocyclic Chem.*, (2001), 38, 853-857].

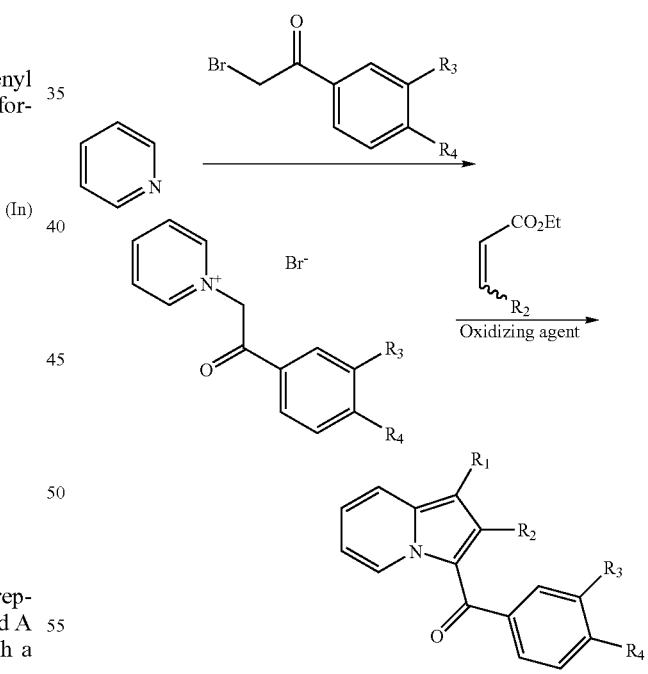

COMPOUNDS (Ia)
A = CO  $R_1$ = CO$_2$Et
$R_2$ = H or AlkXn

The quaternization of pyridine with an appropriately substituted bromoacetophenone gives the pyridinium. The 1,3-dipolar cycloaddition of the latter is carried out in the presence of an oxidizing agent such as tetrapyridinecobalt(II) dichromate, in a polar solvent such as dimethylformamide.

GENERAL SYNTHESIS DIAGRAM

FIG. 2

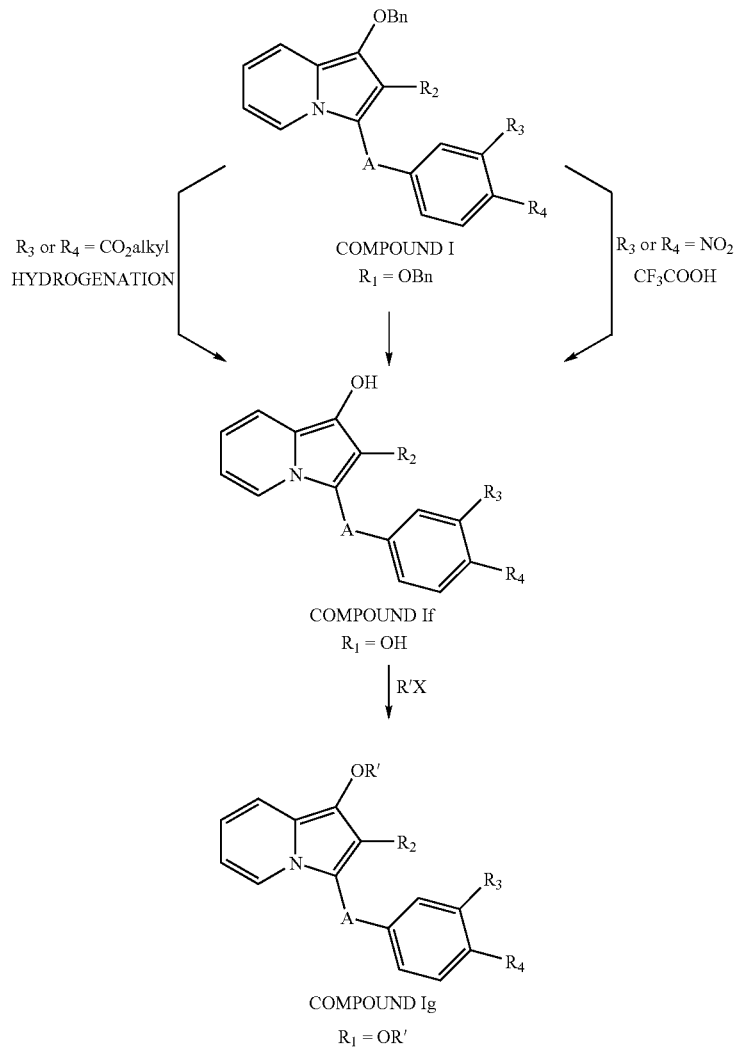

The compounds according to the invention, when $R_3$ and/or $R_4$ represent a nitro radical, are prepared with known benzoylation methods (*Eur. J. Med. Chem. Chim. Ther.*, (1983), 18(4), pp. 339-346) from an indolizine derivative of formula II, and a nitrobenzoyl chloride derivative or a nitrobenzenesulphonyl chloride derivative, which compounds correspond to a compound of formula III. The compounds of formula Ia are thus obtained.

The compounds of formula Ib in which $R_3$ and/or $R_4$ represent an amino radical are obtained from the compounds of formula Ia by reducing the nitro functional group. By subjecting the compounds of formula Ib to the action of an alkyl halide, the compounds of formula Ic are obtained for which $R_3$ and/or $R_4$ represent a radical —$NR_5R_6$ (in which $R_5$ represents a hydrogen atom and $R_6$ has the meanings given above), a radical —NH-Alk-$NR_5R_6$ or a radical —NH-Alk-$COOR_7$ in which $R_7$ does not represent a hydrogen atom. The compounds for which $R_7$ represents a hydrogen atom are obtained from the latter compounds by subjecting them to subsequent saponification.

By acylating the compounds of formula Ib, the compounds of formula Ic are obtained for which $R_3$ and/or $R_4$ represent a radical —NH—CO-Alk or a radical —NH—CO-Alk-$NR_9R_{10}$.

By subjecting these compounds for which $R_3$ and/or $R_4$ represent a radical —NH—CO-Alk or a radical —NH—CO-Alk-$NR_9R_{10}$ to alkylation with a derivative containing an alkoxycarbonyl residue, the compounds of formula I are obtained for which $R_3$ and/or $R_4$ represent a radical —$N(R_{11})$—CO-Alk or a radical —$N(R_{11})$—CO-Alk-$NR_9R_{10}$ where $R_{11}$ represents a radical -Alk-$COOR_{12}$ where $R_{12}$ does not represent a hydrogen atom. By subjecting the latter products to saponification, compounds are obtained for which $R_3$ and/or $R_4$ represent a radical —$N(R_{11})$—CO-Alk or a radical —$N(R_{11})$—CO-Alk-$NR_9R_{10}$ where $R_{11}$ represents a radical -Alk-COOH.

By sulphonylation of the compounds of formula Ib, the compounds of formula Ic are obtained for which $R_3$ and/or $R_4$ represent a radical —NH—$SO_2$-Alk or a radical —NH—$SO_2$-Alk-$NR_9R_{10}$.

By subjecting these compounds for which $R_3$ and/or $R_4$ represent a radical —NH—$SO_2$-Alk or a radical —NH—$SO_2$-Alk-$NR_9R_{10}$ to alkylation with a derivative containing an alkoxycarbonyl residue, the compounds of formula I are obtained for which $R_3$ and/or $R_4$ represent a radical —N($R_{11}$)—$SO_2$-Alk or a radical —N($R_{11}$)—$SO_2$-Alk-$NR_9R_{10}$ where $R_{11}$ represents a radical -Alk-$COOR_{12}$ where $R_{12}$ does not represent a hydrogen atom. By subjecting the latter products to saponification, compounds are obtained for which $R_3$ and/or $R_4$ represent a radical —N($R_{11}$)—$SO_2$-Alk or a radical —N($R_{11}$)—$SO_2$-Alk-$NR_9R_{10}$ where $R_{11}$ represents a radical -Alk-COOH.

By reacting an indolizine derivative of formula II with an alkoxycarbonylbenzoyl chloride derivative of formula III, the compounds of formula Id are obtained in which $R_3$ and/or $R_4$ represent an alkoxycarbonyl radical. By subjecting the latter compounds to saponification, the compounds of formula Ie are obtained in which $R_3$ and/or $R_4$ represent a carboxyl radical.

By reacting an indolizine derivative of formula II with a trifluoroacetamidobenzoyl chloride derivative of formula III, the compounds of formula Ik are obtained in which $R_3$ and/or $R_4$ represent a trifluoroacetamide radical. By subjecting the latter compounds to basic hydrolysis, the compounds of formula Ik are obtained in which $R_3$ and/or $R_4$ represent a carboxyl and/or amino radical.

As represented in FIG. 2, starting with the compounds of formula I in which $R_1$ represents a benzyloxy radical and $R_3$ or $R_4$ represents an alkoxycarbonyl radical, it is possible to obtain, by subjecting these compounds to hydrogenation, the compounds of formula If. When $R_3$ or $R_4$ represents a nitro radical, the compounds of formula If are obtained by the action of trifluoroacetic acid.

By subjecting the compounds of formula If to O-alkylation, the compounds of formula Ig are obtained in which $R_1$ represents a linear or branched alkoxy radical of 1 to 5 carbon atoms, a radical —O—$(CH_2)_n$-cAlk, a radical —O-Alk-$COOR_7$, a radical —O-Alk-$NR_5R_6$, a radical —O—$(CH_2)_n$—Ph, a radical —O-Alk-O—$R_8$— which, when $R_8$ represents a radical —$COCH_3$, can give, by saponification, the radical —O-Alk-OH,—a radical —O-Alk-CN which can give the radical —O-Alk-C($NH_2$):NOH by treating with hydroxylamine.

To obtain the compounds of formula Ih in which $R_1$ is a carboxyl radical and A is a radical —CO— or a radical —$SO_2$, the compounds of formula Ia in which $R_1$ is an alkoxycarbonyl radical are subjected to saponification. The indolizin-1-ylcarboxylic acid derivatives of formula Ih thus obtained can then be subjected to the action of an amine in order to prepare the compounds of formula Ih in which $R_1$ represents a radical —CO—NH-Alk, or to the action of an amino acid derivative in order to obtain the compounds of formula I in which $R_1$ represents a radical —CO—NH—$(CH_2)_m$—$COOR_7$.

The compounds of formula II, when $R_1$ represents a radical —NH—COOtButyl or a radical —N($CH_3$)$CH_2C_6H_5$ are prepared according to the following synthesis schemes using the Tschitschibabin reaction (*Synthesis*, (1975), p. 209) in order to prepare the indolizines.

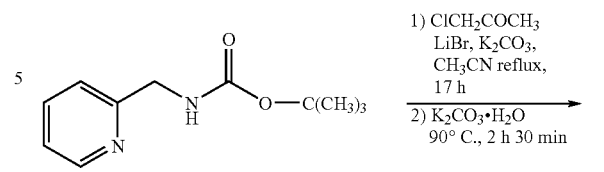

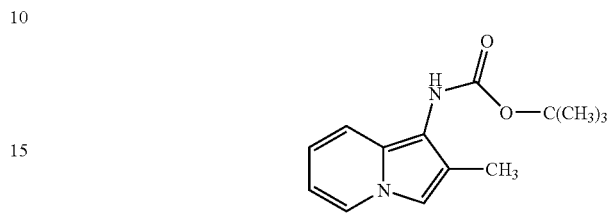

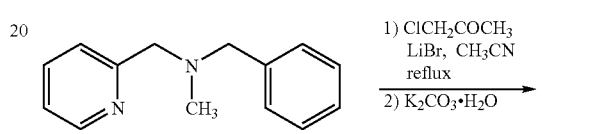

The compounds of formula II, when $R_1$ represents a radical —$OCH_3$ or a radical —$OCH_2C_6H_5$, are also prepared using the Tschitschibabin reaction according to the following synthesis schemes:

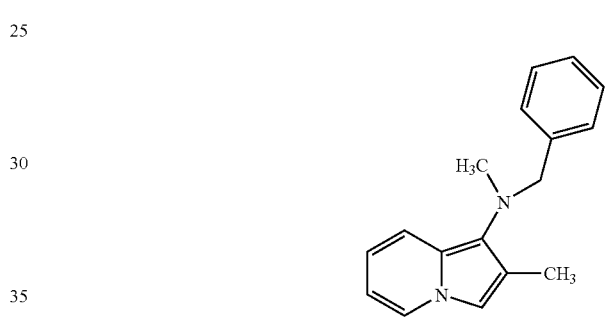

R' = $CH_3$, $CH_2C_6H_5$

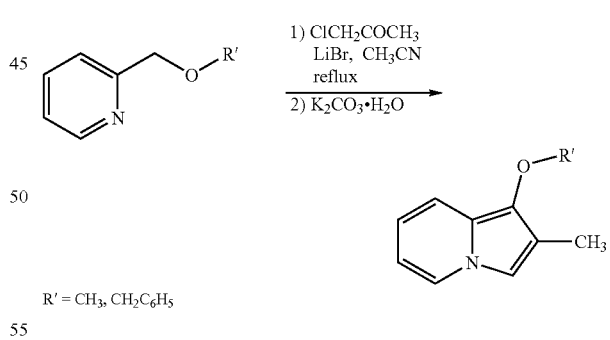

The compounds of formula I are potent antagonists of FGF1 and 2. Their capacities to inhibit both the formation of new vessels from differentiated endothelial cells and to block the differentiation of CD34+ CD133+ adult human bone marrow cells into endothelial cells has been demonstrated in vitro. Furthermore, their capacity to inhibit pathological angiogenesis has been demonstrated in vivo.

In general, the FGFs are greatly involved, via autocrine, paracrine or juxtacrine secretions, in the phenomena of deregulation of the stimulation of the growth of cancer cells. Furthermore, FGFs affect tumour angiogenesis which plays a preponderant role both in the growth of the tumour and also in the phenomena of metastasization.

Angiogenesis is a process of generation of new capillary vessels from preexisting vessels or by mobilization and differentiation of bone marrow cells. Thus, both an uncontrolled proliferation of endothelial cells and a mobilization of angioblasts from the bone marrow are observed in tumour neovascularization processes. It has been shown in vitro and in vivo that several growth factors stimulate endothelial proliferation, and in particular FGF1 or a-FGF and FGF2 or b-FGF. These two factors induce the proliferation, migration and production of proteases by endothelial cells in culture and neovascularization in vivo. a-FGF and b-FGF interact with the endothelial cells via two classes of receptors, the high-affinity receptors with tyrosine kinase activity (FGFRs) and the low-affinity receptors of the heparin sulphate proteoglycan (HSPG) type situated at the surface of the cells and in the extracellular matrices. While the paracrine role of these two factors on endothelial cells is widely described, a-FGF and b-FGF could also act on these cells through an autocrine process. Thus, a-FGF and b-FGF and their receptors represent very suitable targets for therapies aimed at inhibiting the angiogenesis process (Keshet E., Ben-Sasson S. A., *J. Clin. Invest.*, (1999), Vol. 501, pp. 104-1497; Presta M., Rusnati M., Dell'Era P., Tanghetti E., Urbinati C., Giuliani R. et al., *New York: Plenum Publishers*, (2000), pp. 7-34, Billottet C., Janji B., Thiery J. P., Jouanneau J., Oncogene, (2002), Vol. 21, pp. 8128-8139).

Moreover, systematic studies aimed at determining the expression due to a-FGF and b-FGF and their receptors (FGFR) on various types of tumour cells demonstrate that a cellular response to these two F factors is functional in a great majority of human tumour lines studied. These results support the hypothesis that an antagonist of a-FGF and b-FGF could also inhibit the proliferation of tumour cells (Chandler L. A., Sosnowski B. A., Greenlees L., Aukerman S. L., Baird A., Pierce G. F., *Int. J. Cancer*, (1999), Vol. 58, pp. 81-451).

a-FGF and b-FGF play an important role in the growth and maintenance of prostate cells. It has been shown, both in animal models and in humans, that an alteration of the cellular response to these factors plays a crucial role in the progression of prostate cancer. Indeed, in these pathologies, both an increase in the production of a-FGF and b-FGF by the fibroblasts and the endothelial cells present in the tumour and an increase in the expression of the FGFR receptors on tumour cells are recorded. Thus, a paracrine stimulation of prostate cancer cells occurs, and this process could be a major component of this pathology. A compound possessing an FGFR receptor antagonizing activity such as the compounds of the present invention can represent a therapy of choice in these pathologies (Giri D., Ropiquet F., *Clin. Cancer Res.*, (1999), Vol. 71, pp. 5-1063; Doll J. A., Reiher F. K., Crawford S. E., Pins M. R., Campbell S. C., Bouck N. P., *Prostate*, (2001), Vol. 305, pp. 49-293).

Several studies show the presence of a-FGF and b-FGF and of their FGFR receptors both in human breast tumour lines (in particular MCF7) and in biopsies of tumours. These factors could be responsible, in this pathology, for the appearance of the very aggressive phenotype inducing high metastasization. Thus, a compound possessing an FGF receptor antagonizing activity, such as the compounds of formula I, may represent a therapy of choice in these pathologies (Vercoutter-Edouart A-S., Czeszak X., Crépin M., Lemoine J., Boilly B., Le Bourhis X. et al., *Exp. Cell Res.*, (2001), Vol. 262, pp. 59-68).

Cancerous melanomas are tumours which induce metastases at a high frequency and which are very resistant to various chemotherapy treatments. The angiogenesis processes play a preponderant role in the progression of a cancerous melanoma. Furthermore, it has been shown that the probability of the appearance of metastases increases very strongly with the increase in the vascularization of the primary tumour. Melanoma cells produce and secrete various angiogenic factors, including a-FGF and b-FGF. Moreover, it has been shown that inhibition of the cellular effect of these two factors by soluble FGFR1 blocks in vitro the proliferation and the survival of melanoma tumour cells and blocks in vivo tumour progression. Thus, a compound possessing FGFR receptor antagonizing activity, such as the compounds of the present invention, may represent a therapy of choice in these pathologies (Rofstad E. K., Halsor E. F., *Cancer Res.*, (2000); Yayon A., Ma Y-S., Safran M., Klagsbrun M., Halaban R., *Oncogene*, (1997), Vol. 14, pp. 2999-3009).

Glioma cells produce in vitro and in vivo a-FGF and b-FGF and possess various FGFRs at their surface. This therefore suggests that these two factors, through an autocrine and paracrine effect, lay a pivotal role in the progression of this type of tumour. Furthermore, like the majority of solid tumours, the progression of gliomas and their capacity to induce metastases is highly dependent on the angiogenic processes in the primary tumour. It has also been shown that FGFR1 antisenses block the proliferation of human astrocytomas. Furthermore, naphthalenesulphonate derivatives are described for inhibiting the cellular effects of a-FGF and b-FGF in vitro and the angiogenesis induced by these growth factors in vivo. Intracerebral injection of these compounds induces a very significant increase in apoptosis and a substantial decrease in angiogenesis resulting in considerable regression of gliomas in rats. Thus, a compound possessing an antagonist activity for a-FGF and/or b-FGF and/or the FGFR receptors, such as the compounds of the present invention, may represent a therapy of choice in these pathologies (Yamada S. M., Yamaguchi F., Brown R., Berger M. S., Morrison R. S., *Glia*, (1999), Vol. 76, pp. 28-66; Auguste P., Gürsel D. B., Lemière S., Reimers D., Cuevas P., Carceller F., et al., *Cancer Res.*, (2001), Vol. 26, pp. 61-1717).

More recently, the potential role of proangiogenic agents in leukaemias and lymphomas has been documented. Indeed, it has been reported, in general, that cellular clones in these pathologies may be either naturally destroyed by the immune system or switch to an angiogenic phenotype which promotes their survival and then their proliferation. This change of phenotype is induced by an overexpression of angiogenic factors, in particular by the macrophages, and/or mobilization of these factors from the extracellular matrix (Thomas D. A., Giles F. J., Cortes J., Albitar M., Kantarjian H. M., *Acta Haematol*, (2001), Vol. 207, pp. 106-190). Among the angiogenic factors, b-FGF has been detected in numerous lymphoblastic and hematopoietic tumour cell lines. The FGFR receptors are also present on a majority of these lines, suggesting a possible autocrine cellular effect of a-FGF and b-FGF inducing the proliferation of these cells. Moreover, it has been reported that bone marrow angiogenesis by paracrine effects was correlated with the progression of some of these pathologies.

More particularly, it has been shown, in CLL (chronic lymphocytic leukaemia) cells that b-FGF induces an increase in the expression of the antiapoptotic protein (Bc12) leading to an increase in the survival of these cells and therefore greatly participates in their cancerization. Furthermore, the b-FGF levels measured in these cells are very well correlated with the stage of clinical advance of the disease and the resistance to the chemotherapy applied in this pathology (fludarabine). Thus, a compound possessing an FGFR receptor antagonizing activity, such as the compounds of the present invention, may represent a therapy of choice, either in combination with fludarabine or other active products, in this pathology (Thomas D. A., Giles F. J., Cortes J., Albitar M., Kantarjian H. M., *Acta Haematol*, (2001), Vol. 207, pp. 106-190; Gabrilove J. L. *Oncologist*, (2001), Vol. 6, pp. 4-7).

A correlation exists between the process of bone marrow angiogenesis and the extramedullary diseases in CML (chronic myelomonocytic leukaemia). Various studies demonstrate that the inhibition of angiogenesis, in particular by a compound possessing an FGFR receptor antagonizing activity could represent a therapy of choice in this pathology.

The proliferation and the migration of vascular smooth muscle cells contribute to intimal hypertrophy of the arteries and thus plays a preponderant role in atherosclerosis and in restenosis following angioplasty and endarterectomy.

Studies in vivo show, after lesion of the carotid by balloon injury, a local production of a-FGF and b-FGF. In this same model, an anti-FGF2 neutralizing antibody inhibits the proliferation of vascular smooth muscle cells and thus decreases intimal hypertrophy.

A chimeric protein FGF2 bound to a molecule such as saponin blocks the binding of b-FGF to its FGFR receptors, inhibits the proliferation of vascular smooth muscle cells in vitro and intimal hypertrophy in vivo (Epstein C. E., Siegall C. B., Biro S., Fu Y. M., FitzGerald D., *Circulation*, (1991), Vol. 87, pp. 84-778; Waltenberger J., *Circulation*, (1997), pp. 96-4083).

Thus, antagonists of the FGFR receptors, such as the compounds of the present invention, represent a therapy of choice, either alone or in combination with antagonist compounds for other growth factors involved in these pathologies, such as PDGF, in the treatment of pathologies linked to the proliferation of vascular smooth muscle cells such as atherosclerosis, restenosis post-angioplasty or following the fitting of endovascular prostheses (stents) or during aorto-coronary artery by-pass surgery.

Cardiac hypertrophy occurs in response to a stress of the ventricular wall induced by an overload in terms of pressure or volume. This overload may be the consequence of numerous physiopathological states such as hypertension, AC (aortic coarctation), myocardial infarction and various vascular disorders. The consequences of this pathology are morphological, molecular and functional changes such as hypertrophy of cardiac myocytes, the accumulation of matrix proteins and the re-expression of foetal genes. b-FGF is involved in this pathology. Indeed, the addition of b-FGF to cultures of cardiomyocytes of newborn rats modifies the profile of the corresponding genes to contractile proteins leading to a foetal-type gene profile. Additionally, adult rat myocytes show a hypertrophic response under the effect of b-FGF, this response being blocked by anti-b-FGF neutralizing antibodies. Experiments carried out in vivo on transgenic knockout mice for b-FGF show that b-FGF is the major stimulating factor for cardiac myocyte hypertrophy in this pathology (Schultz Je J., Witt S. A., Nieman M. L., Reiser P. J., Engle S. J., Zhou M. et al., *J. Clin. Invest.*, (1999), Vol. 19, pp. 104-709).

Accordingly, a compound, such as the compounds of the present invention, possessing FGFR receptor antagonizing activity represents a therapy of choice in the treatment of cardiac insufficiency and any other pathology associated with a degeneracy of the cardiac tissue. This treatment could be carried out alone or in combination with current treatments (beta-blockers, diuretics, angiotensin antagonists, antiarrhythmics, anti-calcium agents, antithrombotics, and the like).

Vascular disorders caused by diabetes are characterized by an alteration of vascular reactivity and of blood flow, hyperpermeability, an exacerbated proliferative response and an increase in matrix protein deposits. More precisely, a-FGF and b-FGF are present in the preretinal membranes of patients with diabetic retinopathies, in the membranes of underlying capillaries and in the vitreous humour of patients suffering from proliferative retinopathies. A soluble FGF receptor capable of binding both a-FGF and b-FGF is developed in vascular disorders linked to diabetes (Tilton R. G., Dixon R. A. F., Brock T. A., *Exp. Opin. Invest. Drugs*, (1997), Vol. 84, pp. 6-1671). Thus, a compound such as the compounds of formula I possessing an FGFR receptor antagonizing activity represents a therapy of choice either alone or in combination with antagonist compounds for other growth factors involved in these pathologies, such as VEGF.

Rheumatoid arthritis (RA) is a chronic disease with an unknown aetiology. While it affects numerous organs, the most severe form of RA is a progressive synovial inflammation of the joints leading to destruction. Angiogenesis appears to greatly affect the progression of this pathology. Thus, a-FGF and b-FGF have been detected in the synovial tissue and in the joint fluid of patients suffering from RA, indicating that this growth factor is involved in the initiation and/or progression of this pathology. In AIA models (adjuvant-induced model of arthritis) in rats, it has been shown that the overexpression of b-FGF increases the severity of the disease whereas an anti-b-FGF neutralizing antibody blocks the progression of RA (Yamashita A., Yonemitsu Y., Okano S., Nakagawa K., Nakashima Y., Irisa T. et al., *J. Immunol.*, (2002), Vol. 57, pp. 168-450; Manabe N., Oda H., Nakamura K., Kuga Y., Uchida S., Kawaguchi H., *Rheumatol*, (1999), Vol. 20, pp. 38-714). Thus, the compounds according to the invention represent a therapy of choice in this pathology.

IBDs (inflammatory bowel diseases) comprise two forms of chronic inflammatory diseases of the intestine: UC (ulcerative colitis) and Crohn's disease (CD). IBDs are characterized by an immune dysfunction which results in an inappropriate production of inflammatory cytokines inducing the establishment of a local microvascular system. The consequence of this angiogenesis of inflammatory origin is an intestinal ischaemia induced by vasoconstriction. High circulating and local levels of b-FGF were measured in patients suffering from these pathologies (Kanazawa S., Tsunoda T., Onuma E., Majima T., Kagiyama M., Kkuchi K., *American Journal of Gastroenterology*, (2001), Vol. 28, pp. 96-822; Thorn M., Raab Y., Larsson A., Gerdin B., Hallgren R., *Scandinavian Journal of Gastroenterology*, (2000), Vol. 12, pp. 35-408). The compounds of the invention which exhibit a high antiangiogenic activity in a model of inflammatory angiogenesis represent a therapy of choice in these pathologies.

FGFR1, 2 and 3 are involved in the processes of chronogenesis and osteogenesis. Mutations leading to the expression of permanently activated FGFRs have been linked to a large number of human genetic diseases which result in malformations of the skeleton, such as Pfeiffer, Crouzon, Apert, Jackson-Weiss and Beare-Stevenson cutis gyrata syndromes. Some of these mutations, which affect more particularly FGFR3, lead in particular to achondroplasia (ACH), hypochondroplasia (HCH) and TD (Thanatophoric dysplasia), ACH being the most common form of nanism. From a biochemical point of view, sustained activation of these receptors occurs through dimerization of the receptor in the absence of ligand (Chen. L., Adar R., Yang X., Monsonego E. O., LI C., Hauschka P. V., Yagon A. and Deng C. X., (1999), *The Journal of Clin. Invest.*, Vol. 104, No. 11, pp. 1517-1525). Thus, the compounds of the invention which exhibit an antagonist activity on the binding of b-FGF and FGFR and which thus inhibit the dimerization of the receptor represent a therapy of choice in these pathologies.

By virtue of their low toxicity and their pharmacological and biological properties, the compounds of the present invention find application in the treatment of any carcinoma having a high degree of vascularization (lung, breast, prostate, oesophagus) or inducing metastases (colon, stomach, melanoma) or sensitive to a-FGF or to b-FGF in an autocrine manner or, finally, in lymphoma and leukaemia type pathologies. These compounds represent a therapy of choice either alone or in combination with an appropriate chemotherapy. The compounds according to the invention also find application in the treatment of cardiovascular diseases such as atherosclerosis, post-angioplasty restenosis, in the treatment of diseases linked to the complications which appear following the fitting of endovascular prostheses and/or aorto-coronary artery by-passes or other vascular transplants and cardiac hypertrophy or vascular complications of diabetes such as diabetic retinopathies. The compounds according to the invention also find application in the treatment of chronic inflammatory diseases such as rheumatoid arthritis or IBDs. Finally, the compounds according to the invention may be used in the treatment of achondroplasia (ACH), hypochondroplasia (HCH) and TD (thanatrophoric dysplasia).

According to another of its features, the subject of the present invention is therefore a pharmaceutical composition containing, as active ingredient, a compound of formula I according to the invention or one of its pharmaceutically acceptable salts, optionally in combination with one or more inert and appropriate excipients.

The said excipients are chosen according to the pharmaceutical dosage form and the desired mode of administration: oral, sublingual, subcutaneous, intramuscular, intravenous, transdermal, transmucosal, local or rectal.

The pharmaceutical compositions according to the present invention are preferably administered by the oral route.

In the pharmaceutical compositions of the present invention for oral administration, the active ingredients may be administered in a unit form for administration, as a mixture with conventional pharmaceutical carriers. The appropriate unit forms for administration comprise, for example, tablets, which are optionally scored, gelatine capsules, powders, granules and oral solutions or suspensions.

When a solid composition in the form of tablets is prepared, the main active ingredient is mixed with a pharmaceutical vehicle such as gelatine, starch, lactose, magnesium stearate, talc, gum Arabic and the like.

It is possible to coat the tablets with sucrose or other appropriate materials, or alternatively it is possible to treat them so that they have a prolonged or delayed activity and they continuously release a predetermined quantity of active ingredient.

A preparation in the form of gelatine capsules is obtained by mixing the active ingredient with a diluent and pouring the mixture obtained in soft or hard gelatine capsules.

A preparation in syrup or elixir form may contain the active ingredient together with a sweetener, preferably calorie-free, methylparaben and propylparaben as antiseptics, a taste enhancer and an appropriate colouring.

Water-dispersible powders or granules may contain the active ingredient as a mixture with dispersing agents, wetting agents or suspending agents, such as polyvinylpyrrolidone, and with sweeteners or flavour corrigents.

The active ingredient may also be formulated in the form of microcapsules, optionally with one or more carriers or additives.

In the pharmaceutical compositions according to the present invention, the active ingredient may also be in the form of an inclusion complex in cyclodextrins, their ethers or their esters.

The quantity of active ingredient to be administered depends, as always, on the degree of progression of the disease and the age and weight of the patient.

The compositions according to the invention, for oral administration, therefore contain recommended doses of 0.01 to 700 mg.

The following examples, given without limitation, illustrate the present invention.

PREPARATIONS

Preparation I

Synthesis of tert-butyl
2-methylindolizin-1-ylcarbamate 11.7 g (62.4 mmol) of potassium carbonate and 6.3 g of (72 mmol) of lithium bromide are added to 10 g (48 mmol) of tert-butyl [(pyridin-2-yl)methyl]carbamate in 50 ml of acetonitrile, followed by 5 ml (62.4 mmol) of chloroacetone, and the medium is heated under reflux overnight.

It is cooled and 40 ml of water and 11.7 g (62.4 mmol) of potassium carbonate are added, and the medium is heated at 90° C. for 2 h 30 min. The reaction medium is cooled and extracted with ethyl acetate.

The organic phase is removed after settling out, washed with a saturated aqueous sodium chloride solution, dried over sodium sulphate and concentrated under reduced pressure. The product is purified by flash chromatography on a silica column, eluting with a toluene/ethyl acetate (95:5) mixture. 6.27 g of a white powder are collected.

Yield: 53% Melting point: 111° C.

Preparation II

Synthesis of
N-benzyl-N-methyl-N-(2-methylindolizin-1-yl)amine

This compound is obtained according to the same procedure as the compound of Preparation I, using the Tschitschibabin reaction and starting with 2.47 g of N-benzyl-N-methyl-N-[(pyridin-2-yl)methyl]amine and chloroacetone. 970 mg of a yellow oil are obtained.

Yield: 34% Mass spectrometry (ES+ mode): MH+=251

Preparation III

Synthesis of 1-methoxy-2-methylindolizine

This compound is obtained starting with 2-(methoxymethyl)pyridine and chloroacetone, using the Tschitschibabin reaction. The product is isolated in the form of a yellow oil which crystallizes in the freezer.

Yield: 77.5% Mass spectrometry (ES+ mode): MH+=161.8

Preparation IV

Synthesis of 1-benzyloxy-2-methylindolizine

This compound is obtained according to the same procedure as that described in Preparation I using the Tschitschibabin reaction.

The product is isolated in the form of a yellow oil.
Yield: 39%

Preparation V

Synthesis of methyl 5-(chlorocarbonyl)-2[(2,2,2-trifluoroacetyl)amino]benzoate

Step A

Synthesis of 4-amino-3-(methoxycarbonyl)benzoic acid 150 mg (1.21 mmol) of 4-dimethylaminopyridine are added to 2.5 g (12.1 mmol) of 2,4-dioxo-1,4-dihydro-2H-3,1-benzoxazine-6-carboxylic acid [described in *J. Med. Chem.*, (1981), 24(6), 735-742] in solution in 10 ml of dimethylformamide and 10 ml of methanol, and the mixture is heated at 60° C. for 3 hours. The reaction medium is concentrated under reduced pressure. The residue is taken up in water and extracted with ethyl acetate. The organic phase is washed with a saturated sodium chloride solution, dried over sodium sulphate and concentrated under reduced pressure. The solid obtained is taken up in ethyl acetate, filtered and dried. 1.98 g of a white powder are obtained.

Yield: 84% Melting point: 224.5° C.

Step B

Synthesis of methyl 3-(methoxycarbonyl)-4-[(2,2,2-trifluoroacetyl)amino]benzoate 868 μl (6.15 mmol) of trifluoroacetic anhydride are rapidly added to 1.0 g (5.12 mmol) of 4-amino-3-(methoxycarbonyl) benzoic acid in suspension in 15 ml of dichloromethane. The solution is stirred for 30 minutes at room temperature. The solution is concentrated to dryness and the solid obtained is taken up in a pentane/ethyl ether mixture and then filtered off. 1.48 g of a white powder are obtained after drying.

Yield: 99% Melting point: 239° C.

Step C

530 μl (7.27 mmol) of thionyl chloride and 3 drops of dimethylformamide are added to 784 mg (2.69 mmol) of methyl 3-(methoxycarbonyl)-4-[(2,2,2-trifluoroacetyl) amino]benzoate in solution in 9 ml of dichloromethane, and then the medium is heated under reflux for 90 minutes. It is evaporated to dryness, and the excess of thionyl chloride is carried away by coevaporation with toluene. 834 mg of acid chloride are obtained in the form of a yellow solid, which solid is used as is it without further purification in the steps of benzoylation of the indolizines.

Yield: quantitative.

EXAMPLES

Example 1

(1-Methoxy-2-methylindolizin-3-yl)(3-methoxy-4-nitrophenyl)methanone 4.21 g (0.0195 mol) of 3-methoxy-4-nitrobenzoyl chloride are added to 3 g (0.0186 mol) of 1-methoxy-2-methylindolizine whose preparation is described in Preparation III, dissolved in 50 ml of 1,2-dichloroethane, and the medium is stirred at room temperature for 4 hours.

The reaction medium is poured over water. The organic phase is separated after settling out, washed with an aqueous sodium bicarbonate solution and then with water, dried over sodium sulphate and concentrated under vacuum.

The residue is purified by chromatography on a silica column, eluting with dichloromethane. After evaporation, 6.05 g of a yellow solid are obtained.

Yield: 95% Melting point: 287° C.

Examples 2 to 28

By carrying out the procedure according to the preparation described above, the compounds of formula I, for which A represents a radical —CO—, which are described in Table I below, are synthesized by benzoylation of the 3-position of the indolizines variously substituted at the 1- and 2-positions with suitably substituted benzoyl chlorides.

TABLE I

| Example | $R_1$ | $R_2$ | $R_3$ | $R_4$ | Yield (%) | Melting point (° C.) or mass spectrometry (MH+) |
|---|---|---|---|---|---|---|
| 2  | OBn     | Ph  | OMe      | $NO_2$       | 94   | 186° C. |
| 3  | OBn     | Me  | OMe      | $NO_2$       | 95   | 153° C. |
| 4  | OBn     | Me  | H        | $CO_2Me$     | 70.5 | 110° C. |
| 5  | OMe     | cPr | OMe      | $NO_2$       | 81   | 112° C. |
| 6  | OMe     | Ph  | OMe      | $NO_2$       | 82   | 65° C.  |
| 7  | OMe     | Me  | H        | $NO_2$       | 88   | 146° C. |
| 8  | OMe     | Me  | H        | $CO_2Me$     | 92   | 143° C. |
| 9  | OMe     | Me  | $CO_2Me$ | H            | 75   | 121° C. |
| 10 | OMe     | Me  | $NO_2$   | $CO_2Me$     | 57   | 138° C. |
| 11 | OMe     | Me  | OMe      | $CO_2Me$     | 88.5 | 145° C. |
| 12 | OMe     | Me  | H        | $CH_2CO_2Me$ | 75   | 94° C.  |
| 13 | $CO_2Et$| Me  | OMe      | —$NO_2$      | 91   | 137° C. |
| 14 | $CO_2Et$| Me  | OMe      | $CO_2Me$     | 45.5 | 141° C. |
| 15 | $CO_2Et$| Ph  | OMe      | $NO_2$       | 85   | 151° C. |
| 16 | $CO_2Et$| Me  | H        | $CO_2Me$     | 98   | 139° C. |
| 17 | N(Me)Bn | Me  | OMe      | $NO_2$       | 90   | MH+ = 430.3 |
| 18 | NHBOC   | Me  | OMe      | $NO_2$       | 76   | MH+ = 426.5 |
| 19 | $CO_2Et$| Me  | $CO_2Me$ | $NO_2$       | 92   | 137° C. |
| 20 | OMe     | Me  | $CO_2Me$ | $NO_2$       | 100  | 150° C. |
| 21 | OMe     | Me  | $NO_2$   | OMe          | 90   | 135° C. |
| 22 | $CO_2Et$| Me  | $NO_2$   | OMe          | 30   | 60° C.  |
| 23 | $CO_2Et$| Me  | $CO_2Me$ | $NO_2$       | 92   | 137° C. |
| 24 | OMe     | Me  | $CO_2Me$ | OMe          | 69   | 119° C. |
| 25 | $CO_2Et$| Me  | $CO_2Me$ | OMe          | 12   | 110° C. |
| 26 | OMe     | cPr | $CO_2Me$ | $NO_2$       | 34   | MH+ = 395.2 |
| 27 | NH—BOC  | Me  | $CO_2Me$ | $NO_2$       | 81   | 92° C.  |
| 28 | NH—BOC  | Me  | $CO_2Me$ | $NHCOCF_3$   | 81   | 226° C. |

Bn = benzyl
Me = methyl
Et = ethyl
BOC = tbutoxycarbonyl

Example 29

(1-Amino-2-methylindolizin-3-yl)(3-methoxy-4-nitrophenyl)methanone 2.32 ml of trifluoroacetic acid are added dropwise to a solution of 643 mg (1.51 mmol) of tert-butyl 3-(3-methoxy-4-nitrobenzoyl)-2-methylindolizin-1-ylcarbamate in 20 ml of dichloromethane, cooled to 0° C. Once the introduction is complete, the medium is allowed to return to room temperature and it is stirred for 4 hours. The reaction medium is poured over a saturated aqueous potassium carbonate solution and extracted with ethyl acetate. The organic phase is separated after settling out, washed with a saturated aqueous sodium chloride solution, dried over sodium sulphate and concentrated under reduced pressure. The crystals obtained are taken up in isopropyl ether, filtered off, washed with isopropyl ether and then dried. 425 mg of a brown solid are obtained.

Yield: 87% Mass spectrometry (ES+ mode) MH$^+$=326.3

By carrying out the procedure according to the preparation described above, the compounds of formula I, for which A represents a radical —CO— and which are described in Table II below, are synthesized by deprotecting the amine at the 1-position of the indolizines with the aid of trifluoroacetic acid.

TABLE II

| Example | R$_1$ | R$_2$ | R$_3$ | R$_4$ | Yield (%) | Melting point (° C.) |
|---|---|---|---|---|---|---|
| 30 | NH$_2$ | Me | CO$_2$Me | NO$_2$ | 91 | 162° C. |
| 31 | NH$_2$ | Me | CO$_2$Me | NHCOCF$_3$ | 88 | 231° C. |

Example 32

N-[3-(3-Methoxy-4-nitrobenzoyl)-2-methylindolizin-1-yl]methanesulphonamide 0.292 ml (3.78 mmol) of mesyl chloride is added to a solution of 350 mg (1.08 mmol) of the compound of Example 29 in 3 ml of pyridine, and the medium is stirred at room temperature for 4 hours. The reaction medium is concentrated under reduced pressure. The residue is taken up in 1 N hydrochloric acid and extracted with dichloromethane. The organic phase is separated after settling out, washed with a saturated aqueous sodium chloride solution, dried over sodium sulphate and concentrated under reduced pressure. The residue is crystallized from ethanol. 327 mg of yellow crystals are obtained.

Yield: 75% Mass spectrometry (ES+ mode) MH$^+$=404.3

Example 33

Methyl 5-[(1-{[(3-methoxyphenyl)sulphonyl]amino}-2-methylindolizin-3-yl)carbonyl]-2-[(2,2,2-trifluoroacetyl)amino]benzoate This compound is prepared according to the same method as the preceding example, by sulphonylation of methyl 5-[(1-amino-2-methylindolizin-3-yl)carbonyl]-2-[2,2,2-trifluoroacetyl)amino]benzoate with 3-methoxybenzenesulphonyl chloride. 466 mg of a yellow powder are obtained.

Yield: 83% Melting point: 220.5° C.

Example 34

Methyl 5-[(1-{[(3-methoxyanilino)carbonylamino}-2-methylindolizin-3-yl)carbonyl]-2-[(2,2,2-trifluoroacetyl)amino]benzoate 140 µl (1.05 mmol) of 3-methoxyphenyl isocyanate are added to 400 mg (0.95 mmol) of methyl 5-[(1-amino-2-methylindolizin-3-yl)carbonyl]-2-[2,2,2-trifluoroacetyl)amino] benzoate dissolved in 13 ml of tetrahydrofuran. The reaction mixture is heated at 40° C. for 20 hours and concentrated under reduced pressure. The residue obtained is taken up in acetone, the solid is filtered off and it is washed with acetone and then ethyl ether. 442 mg of a yellow powder are obtained.

Yield: 82% Melting point: 314° C.

Example 35

(3-Methoxy-4-nitrophenyl)[2-methyl-1-(methylamino)indolizin-3-yl]methanone

Step A

Synthesis of tert-butyl 3-(3-methoxy-4-nitrobenzoyl)-2-methylindolizin-1-yl(methyl)carbamate 3.05 g (7.2 mmol) of tert-butyl 3-(3-methoxy-4-nitrobenzoyl)-2-methylindolizin-1-ylcarbamate in solution in 50 ml of tetrahydrofuran are added dropwise to 315 mg (7.9 mmol) of sodium hydride (at 60% as a dispersion in oil) in suspension in 10 ml of tetrahydrofuran, cooled to 0° C. After stirring for 1 hour at 0° C., 0.59 ml (9.5 mmol) of methyl iodide is added while the medium is maintained at 0° C. It is allowed to return to room temperature and it is stirred for 1 hour. The reaction medium is poured over a saturated aqueous sodium bicarbonate solution and extracted with ethyl acetate. The organic phase is separated after settling out, washed with a saturated aqueous sodium chloride solution, dried over sodium sulphate and concentrated under reduced pressure. 3.47 g of an orange-coloured foam are obtained.

Yield: 96% Mass spectrometry (ES+ mode) MH$^+$=440.3

Step B 13 ml of trifluoroacetic acid are added dropwise to a solution of 3.38 g (7.7 mmol) of the product obtained in Step A in 60 ml of dichloromethane, cooled to 0° C. When the introduction is complete, the medium is allowed to return to room temperature and it is stirred for 3 hours.

The reaction medium is poured over a saturated aqueous sodium bicarbonate solution and extracted with ethyl acetate. The organic phase is separated after settling out, washed with a saturated aqueous sodium chloride solution, dried over sodium sulphate and concentrated under reduced pressure.

The residue is purified by flash chromatography on a silica column, eluting with a toluene/ethyl acetate (9/1) mixture. After evaporation, 2.2 g of a red powder are obtained.

Yield: 76% Mass spectrometry (ES+ mode) MH$^+$=340.2

Examples 36 and 37

By carrying out the procedure according to Example 35—Step A, the compounds of formula I, for which A represents a radical —CO— and which are described in the Table below, are synthesized by alkylating the tert-butyl carbamate at the 1-position of the indolizines with 3-methoxybenzyl chloride, in the presence of sodium hydride in a solvent such as tetrahydrofuran and dimethylformamide.

TABLE III

| Example | $R_1$ | $R_2$ | $R_3$ | $R_4$ | Yield (%) | Melting point (° C.) or mass spectro. (MH+) |
|---|---|---|---|---|---|---|
| 36 | N(BOC)Bn-3-OMe | Me | OMe | $NO_2$ | 91 | MH+ = 546.4 |
| 37 | N(BOC)Bn-3-OMe | Me | $CO_2Me$ | $NO_2$ | 80 | 65° C. |

Examples 38 and 39

By carrying out the procedure according to Example 35—Step B, the compounds of formula I, for which A represents a radical —CO— and which are described in Table IV below, are synthesized by deprotecting the amine at the 1-position of the indolizines with the aid of trifluoroacetic acid.

TABLE IV

| Example | $R_1$ | $R_2$ | $R_3$ | $R_4$ | Yield (%) | Mass spectro. (MH+) |
|---|---|---|---|---|---|---|
| 38 | NHBn-3-OMe | Me | OMe | $NO_2$ | 89 | MH+ = 446.3 |
| 39 | NHBn-3-OMe | Me | $CO_2Me$ | $NH_2$ | 99 | MH+ = 444.4 |

Example 40

[1-(Dimethylamino)-2-methylindolizin-3-yl](3-methoxy-4-nitrophenyl)methanone 382 mg (1.1 mmol) of the compound of Example 21 in solution in 10 ml of tetrahydrofuran are added dropwise to 44 mg (1.1 mmol) of sodium hydride (at 60% in a dispersion in oil) in suspension in 5 ml of tetrahydrofuran, cooled to 0° C. Once the introduction is complete, the medium is allowed to return to room temperature over 1 hour, and then 69 µl (1.1 mmol) of methyl iodide are added and the medium is stirred at room temperature for 17 hours.

The reaction medium is poured over a saturated aqueous sodium chloride solution and extracted with ethyl acetate. The organic phase is separated after settling out, washed with a saturated aqueous sodium chloride solution, dried over sodium sulphate and concentrated under reduced pressure.

The residue is purified by chromatography on a silica column, eluting with a toluene/ethyl acetate (95/5) mixture. 143 mg of an orange-coloured foam are obtained.
Yield: 37%

Example 41

{1-[(3-Methoxybenzyl)(methyl)amino]-2-methylindolizin-3-yl}(3-methoxy-4-nitrophenyl)methanone 595 mg (1.83 mmol) of caesium carbonate and 83 µl (1.34 mmol) of methyl iodide are added to 542 mg (1.22 mmol) of {1-[(3-methoxybenzyl)amino]-2-methylindolizin-3-yl}(3-methoxy-4-nitrophenylmethanone in solution in 15 ml of dimethylformamide.

The reaction mixture is heated at 40° C. for 21 hours.

The mixture is poured into a saturated sodium chloride solution and extracted with ethyl acetate. The organic phase is dried over sodium sulphate and concentrated under reduced pressure.

The product is purified by chromatography on silica gel, eluting with a toluene/ethyl acetate (95/5) mixture. A red gum is obtained.

Yield: 96% Mass spectrometry (ES+ mode) MH+=460.3

Example 42

Methyl 2-amino-5-({1-[3-methoxybenzyl)(methyl)amino]-2-methylindolizin-3-yl}carbonyl)benzoate This compound is prepared according to the same method as that described in the example above, starting with 340 mg (0.76 mmol) of methyl 2-amino-5-({1-[(3-methoxybenzyl)amino]-2-methylindolizin-3-yl}carbonyl)benzoate. 260 mg of an orange-coloured solid are obtained.
Yield: 80% Melting point: 60° C.

Example 43

Methyl 5-({1-[(3-methoxybenzoyl)amino]-2-methylindolizin-3-yl}carbonyl)-2-[2,2,2-trifluoroacetyl)amino]benzoate 3.37 g (7.6 mmol) of benzotriazol-1-yloxytris(dimethylamino)phosphonium hexafluorophosphate (BOP) and 2.1 ml of triethylamine are added to 1.16 g (7.6 mmol) of 3-methoxybenzoic acid dissolved in 30 ml of dimethylformamide and 60 ml of dichloromethane.

The medium is stirred at room temperature for 15 minutes and then 3.04 g (7.2 mmol) of methyl 5-[(1-amino-2-methylindolizin-3-yl)carbonyl]-2-[2,2,2-trifluoroacetyl)amino]benzoate are added.

After stirring for 16 hours at room temperature, the yellow precipitate obtained in the reaction medium is filtered off and it is washed with dichloromethane. 2.38 g of a yellow powder are obtained.
Yield: 60% Melting point: 239° C.

Examples 44 to 61

By carrying out the procedure according to the method described above, the compounds described in Table V below are synthesized by coupling (1-amino-2-methylindolizin-3-yl)(3-methoxy-4-nitrophenyl)methanone or methyl 5-[(1-amino-2-methylindolizin-3-yl)carbonyl]-2-[2,2,2-trifluoroacetyl)amino]benzoate with the appropriate carboxylic acid in the presence of benzotriazol-1-yloxy-tris(dimethylamino)phosphonium hexafluorophosphate (BOP).

TABLE V

| Example | $R_1$ | $R_2$ | $R_3$ | $R_4$ | Yield (%) | Melting point (° C.) |
|---|---|---|---|---|---|---|
| 44 | NHCOPh-4-Cl | Me | OMe | $NO_2$ | 76 | 255° C. |
| 45 | NHCOPh-4-$CO_2Me$ | Me | OMe | $NO_2$ | 88 | 274° C. |
| 46 | NHCOPh-3-OMe | Me | OMe | $NO_2$ | 86 | 180° C. |
| 47 | NHCOPh-3-OMe-4-$NO_2$ | Me | OMe | $NO_2$ | 60 | 286° C. |

TABLE V-continued

| Example | R$_1$ | R$_2$ | R$_3$ | R$_4$ | Yield (%) | Melting point (° C.) |
|---|---|---|---|---|---|---|
| 48 | NHCOPh-2,3-OMe | Me | CO$_2$Me | NHCOCF$_3$ | 87 | 215° C. |
| 49 | NHCOPh-2,5-OMe | Me | CO$_2$Me | NHCOCF$_3$ | 83 | 214° C. |
| 50 | NHCOPh-3,4-OMe | Me | CO$_2$Me | NHCOCF$_3$ | 76 | 260° C. |
| 51 | NHCOPh-3,4,5-OMe | Me | CO$_2$Me | NHCOCF$_3$ | 83 | 259° C. |
| 52 | NHCOPh-3,5-OMe | Me | CO$_2$Me | NHCOCF$_3$ | 74 | 223° C. |
| 53 | NHCOPh-3-OMe 4-Me | Me | CO$_2$Me | NHCOCF$_3$ | 82 | 251° C. |
| 54 | NHCOPh-3,4-methylenedioxy | Me | CO$_2$Me | NHCOCF$_3$ | 79 | 245° C. |
| 55 | NHCOPh-3-OMe 4-Cl | Me | CO$_2$Me | NHCOCF$_3$ | 82 | 264° C. |
| 56 | NHCOPh-3-OMe 4-F | Me | CO$_2$Me | NHCOCF$_3$ | 27 | 260° C. |
| 57 | NHCOPh-2,5-OMe 4-Cl | Me | CO$_2$Me | NHCOCF$_3$ | 82 | 242° C. |
| 58 | NHCO-5-indolyl | Me | CO$_2$Me | NHCOCF$_3$ | 76 | 186° C. |
| 59 | NHCOPh-3-OMe 4-CO$_2$Me | Me | CO$_2$Me | NHCOCF$_3$ | 77 | 191° C. |
| 60 | NHCOPh-3-OCF$_3$ | Me | CO$_2$Me | NHCOCF$_3$ | 60 | 258° C. |
| 61 | NHCOPh-2.4.5-OMe | Me | CO$_2$Me | NHCOCF$_3$ | 64 | 253° C. |

Example 62

N-[3-(3-Methoxy-4-nitrobenzoyl)-2-methylindolizin-1-yl]acetamide 1.20 ml (12.60 mmol) of acetic anhydride are added to 410 mg (1.26 mmol) of (1-amino-2-methylindolizin-3-yl)(3-methoxy-4-nitrophenyl)methanone dissolved in 10 ml of dichloromethane.

The reaction mixture is stirred at room temperature for 15 minutes. The precipitate obtained is filtered off and washed with ethyl ether and then dried to give 295 mg of an orange-coloured powder.

Yield: 63% Melting point: 238° C.

Example 63

3-Methoxy-N-[3-(3-methoxy-4-nitrobenzoyl)-2-methylindolizin-1-yl]-N-methylbenzamide 51 mg of sodium hydride (60% suspension in oil) are added to 466 mg (1.01 mmol) of 3-methoxy-N-[3-(3-methoxy-4-nitrobenzoyl)-2-methylindolizin-1-yl]benzamide in solution in 19 ml of tetrahydrofuran.

The medium is stirred at room temperature for 10 minutes and then 65 µl of methyl iodide are added. After stirring for 2 hours, water is added to the reaction medium and then the medium is extracted with ethyl acetate. The organic phase is washed with a saturated sodium chloride solution, dried over sodium sulphate and concentrated under reduced pressure.

The product is purified by chromatography on silica gel, eluting with dichloromethane. 435 mg of a yellow solid are obtained.

Yield: 91% Melting point: 190° C.

Example 64

Methyl 5-({1-[(3-methoxybenzoyl)(methyl)amino]-2-methylindolizin-3-yl}carbonyl)-2-nitrobenzoate This compound is prepared according to the protocol described in the example above by methylating 1.9 g (3.9 mmol) of methyl 5-({1-[(3-methoxybenzoyl)amino]-2-methylindolizin-3-yl}carbonyl)-2-nitrobenzoate with methyl iodide. 1.85 g of a red solid are obtained.

Yield: 84% Melting point: 158.5° C.

Example 65

Ethyl [3-(3-methoxy-4-nitrobenzoyl)-2-(trifluoromethyl)indolizin-1-yl]carboxylate Step A Synthesis of 1-[2-(3-methoxy-4-nitrophenyl)-2-oxoethyl]pyridinium bromide 467 µl (5.78 mmol) of pyridine are added to 1.32 g (4.82 mmol) of 2-bromo-1-(3-methoxy-4-nitrophenyl)-1-ethanone, described in Bull. Soc. Chim. Fr., (1962), 2255-2261, in solution in 13 ml of acetonitrile, and the medium is stirred at room temperature for 5 hours.

The reaction medium is precipitated.

Ethyl ether is added, the crystals are filtered off, washed with ethyl ether and then dried. 1.65 g of yellow crystals are obtained.

Yield: 97% Melting point: 216° C.

Step B 500 mg (1.42 mmol) of 1-[2-(3-methoxy-4-nitrophenyl)-2-oxoethyl]pyridinium bromide are added, in portions, to 219 µl (1.56 mmol) of triethylamine in 4.5 ml of dimethylformamide, followed by 1.06 ml (7.08 mmol) of ethyl 4,4,4-trifluorocrotonate and 561 mg (0.92 mmol) of tetrapyridinecobalt (II) dichromate.

The reaction medium is heated at 90° C. for 6 hours. The reaction medium is cooled and then poured over 1 N hydrochloric acid and the product thus obtained is extracted with ethyl acetate.

The organic phase is separated after settling out, washed with water and then with a saturated aqueous sodium chloride solution, dried over sodium sulphate and concentrated under reduced pressure.

The product obtained is purified by chromatography on a silica column, eluting with dichloromethane. 437 mg of a yellow powder are obtained.

Yield: 71% Melting point: 63° C.

Example 66

Ethyl [3-(3-methoxy-4-nitrobenzoyl)indolizin-1-yl]carboxylate

This compound is obtained according to the same method as the preceding example in Step B by 1,3-dipolar cycloaddition of 1-[2-(3-methoxy-4-nitrophenyl)-2-oxoethyl]pyridinium bromide (obtained in Step A of the preceding example) with ethyl acrylate. A yellow powder is obtained after purification by flash chromatography on a silica column, eluting with dichloromethane.

Yield: 78% Melting point: 168° C.

Example 67

(1-Hydroxy-2-methylindolizin-3-yl)(3-methoxy-4-nitrophenyl)methanone

A solution of 5 g (12 mmol) of [1-(benzyloxy-2-methylindolizin-3-yl](3-methoxy-4-nitrophenyl)methanone, a compound of Example 3, in 30 ml of trifluoroacetic acid, is heated under reflux for 2 hours.

The reaction medium is evaporated under reduced pressure. The residue is taken up in ethyl acetate, washed with an aqueous sodium bicarbonate solution and with water, and then the organic phase is dried over sodium sulphate and evaporated under reduced pressure.

The product obtained is purified by chromatography on a silica column, eluting with a dichloromethane/methanol (99/1) mixture. 2.93 g of an orange-coloured powder are obtained.

Yield: 75% Melting point: 193° C.

Example 68

Methyl 4-({[3-(3-methoxy-4-nitrobenzoyl)-2-methylindolizin-1-yl]oxy}methyl)benzoate 812 mg (3.37 mmol) of methyl 4-(bromomethyl)benzoate are added to a solution of 1 g (3.06 mmol) of (1-hydroxy-2-methyl-3-indolizinyl)(3-methoxy-4-nitrophenyl)methanone in 16 ml of dimethylformamide, in the presence of 508 mg (3.68 mmol) of potassium carbonate, and the medium is heated at 90° C. for 4 hours.

The reaction medium is poured over water and extracted with ethyl acetate.

The organic phase is washed with water, dried over sodium sulphate and evaporated to dryness. The product obtained is purified by chromatography on a silica column, eluting with a toluene/ethyl acetate (9/1) mixture. 880 mg of a yellow powder are obtained.

Yield: 60.5% Melting point: 154° C.

Examples 69 to 84

By carrying out the procedure according to the method described in Example 68, the compounds described in Table VI below are synthesized by alkylating (1-hydroxy-2-methylindolizin-3-yl)(3-methoxy-4-nitrophenyl)methanone with appropriately chosen halogenated derivatives. To obtain the compound of Example 80, the compound of Example 79 is subjected to saponification.

TABLE VI

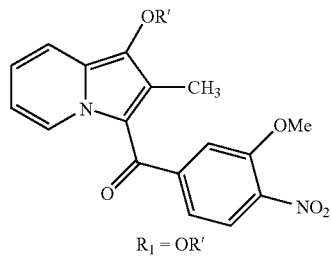

$R_1 = OR'$

Compounds of formula Ia

| Example | R' | Yield (%) | Melting point |
|---|---|---|---|
| 69 | $CH_2C_6H_5$—2Cl | 90 | 173° C. |
| 70 | $CH_2C_6H_5$—3Cl | 74 | 179° C. |
| 71 | $CH_2C_6H_5$—4Cl | 82 | 162° C. |
| 72 | $CH_2C_6H_5$—2OMe | 84 | 148° C. |
| 73 | $CH_2C_6H_5$—3OMe | 67.5 | 145° C. |
| 74 | $CH_2C_6H_5$—4OMe | 71 | 135° C. |
| 75 | $CH_2C_6H_5$—3$CO_2$Me | 57 | 171° C. |
| 76 | $CH_2CO_2Et$ | 91 | 127° C. |
| 77 | $CH_2CONH_2$ | 65 | 222° C. |
| 78 | $(CH_2)_2NMe_2$ | 26 | 108° C. |
| 79 | $(CH_2)_2OAc$ | 68 | Oil |
| 80 | $(CH_2)_2OH$ | 90 | 142° C. |
| 81 | $CH_2CN$ | 91.5 | 176° C. |
| 82 | iPr | 19 | 283° C. |
| 83 | $CH_2cPr$ | 22 | 111° C. |
| 84 | $CH_2C_6H_5$-2-$CO_2$Me | 82 | 146° C. |

Example 85

Methyl 4-[(1-hydroxy-2-methylindolizin-3-yl)carbonyl]benzoate 8.75 ml (86.37 mmol) of cyclohexene are added to 3.45 g (8.64 mmol) of methyl 4-[(1-(benzyloxy)-2-methylindolizin-3-yl)carbonyl]benzoate in 40 ml of ethanol, in the presence of 690 mg of 10% Pd/C, and the medium is heated under reflux for one hour.

The reaction medium is cooled to room temperature and the catalyst is removed by filtration on talc. The filtrate is under reduced pressure.

The product obtained is purified by chromatography on a silica column, eluting with a dichloromethane/methanol (98/2) mixture. 2.5 g of an orange-coloured powder are obtained.

Yield: 93.5% Melting point: 192° C.

Example 86

Methyl 4-{[1-(2-ethoxy-2-oxoethoxy)-2-methylindolizin-3-yl]carbonyl}benzoate

202 µl (1.78 mmol) of ethyl bromoacetate are added to 500 mg (1.62 mmol) of methyl 4-[(1-hydroxy-2-methylindolizin-3-yl)carbonyl]benzoate, a compound of Example 85, in 10 ml of dimethylformamide, in the presence of 268 mg (1.94 mmol) of potassium carbonate, and the medium is heated at 90° C. for one hour.

The reaction medium is cooled, poured over water and extracted with ethyl acetate, and then separated after settling out. The organic phase is washed with water, dried over sodium sulphate and evaporated under reduced pressure. The product obtained is purified by chromatography on a silica column, eluting with a toluene/ethyl acetate (9/1) mixture. 570 mg of a yellow powder are obtained.

Yield: 89% Melting point: 84.5° C.

Example 87

Methyl 4-({1-[(3-methoxybenzyl)oxy]-2-methylindolizin-3-yl}carbonyl)benzoate

This compound is obtained according to the same procedure as that of Example 86, by O-alkylation of methyl 4-[(1-hydroxy-2-methylindolizin-3-yl)carbonyl]benzoate with 3-methoxybenzyl bromide. A yellow powder is obtained which melts at 106° C.

Yield: 76%

Example 88

3-(3-Methoxy-4-nitrobenzoyl)-2-methylindolizin-1-ylcarboxylic acid 26.2 ml of 1 N sodium hydroxide are added to 5 g (13.1 mmol) of ethyl 3-(3-methoxy-4-nitrobenzoyl)-2-methylindolizin-1-ylcarboxylate, a compound of Example 13—prepared according to the procedure of Example 1 by benzoylation of ethyl (2-methylindolizin-1-yl)carboxylate described in *J. Chem. Soc.*, (1963), pp. 3277-3280—, in suspension in 50 ml of dioxane, and the medium is heated under reflux for 17 hours. The reaction medium is concentrated under reduced pressure. The residue is taken up in water, washed with ethyl ether, and the medium is separated after settling out. The aqueous phase is acidified to pH 6 with a potassium hydrogen sulphate solution and extracted with ethyl acetate. The organic phase is washed with water, dried over sodium sulphate and concentrated under reduced pressure. 4.9 g of an orange-coloured powder are obtained.

Yield: quantitative Melting point: 215° C.

Example 89

N-Ethyl 3-(3-methoxy-4-nitrobenzoyl)-2-methylindolizin-1-ylcarboxamide 0.61 ml (4.34 mmol) of triethylamine is added to a solution of 750 mg (2.12 mmol) of the acid of Example 88 in 12 ml of dimethylformamide, followed, in portions, by 983 mg (2.22 mmol) of benzotriazol-1-yloxytris(dimethylamino)phosphonium hexafluorophosphate. The medium is stirred for 5 min at room temperature and then 182 mg (2.22 mmol) of ethylamine hydrochloride are added.

The reaction medium is stirred overnight at room temperature, poured over water and extracted with ethyl acetate. The organic phase is separated after settling out, washed with water, dried over sodium sulphate and concentrated under reduced pressure.

The product is purified by chromatography on a silica column, eluting with dichloromethane/methanol (98/2). 700 mg of a yellow powder are obtained.

Yield: 87% Melting point: 188° C.

Example 90

Ethyl 2-({[3-(3-methoxy-4-nitrobenzoyl)-2-methylindolizin-1-yl]carbonyl}amino)acetate This compound is obtained according to the same method as the preceding compound, by coupling 3-(3-methoxy-4-nitrobenzoyl)-2-methylindolizin-1-ylcarboxylic acid with ethyl glycinate hydrochloride.

The product is purified by chromatography on a silica column, eluting with dichloromethane/methanol (93/7). A yellow powder is obtained.

Yield: 86% Melting point: 191° C.

Example 91

1-Methoxy-2-methyl-3-[(4-nitrophenyl)sulphonyl]indolizine 690 mg (3.1 mmol) of 4-nitrobenzenesulphonyl chloride in solution in 4 ml of 1,2-dichloroethane are added to 500 mg (3.1 mmol) of 1-methoxy-2-methylindolizine dissolved in 8 ml of 1,2-dichloroethane, and the medium is stirred at room temperature for 20 hours. The reaction medium is poured over water and dichloromethane. The organic phase is separated after settling out, washed with water, dried over sodium sulphate and concentrated under reduced pressure.

The product is purified by chromatography on a silica column, eluting with cyclohexane/ethyl acetate (9/1). 330 mg of a yellow oil are obtained.

Yield: 31%

Example 92

1-Methoxy-2-methyl-3-[(3-nitrophenyl)sulphonyl]indolizine

This compound is prepared according to the protocol described for the example above, by sulphonylation of 1 g (6.2 mmol) of 1-methoxy-2-methylindolizine with 3-nitrobenzenesulphonyl chloride. 540 mg of a yellow oil are obtained.

Yield: 98%

Example 93

Sodium salt of 4-[(1-methoxy-2-methylindolizin-3-yl)sulphonyl]benzoic acid

This compound is obtained according to the same procedure as the compound of Example 91, by sulphonylation of 1-methoxy-2-methylindolizine with 4-chlorosulphonylbenzoic acid. The product is purified by flash chromatography on a silica column, eluting with dichloromethane/acetone (9/1). 120 mg of a yellow powder are obtained.

Yield: 11%

The product, dissolved in methanol, is salified by adding one equivalent of 1 N sodium hydroxide. The methanol is evaporated off and the residue is crystallized from acetone. The product is filtered, washed with acetone and then with ethyl ether and dried. 100 mg of sodium salt are obtained in the form of a yellow powder.

Melting point: 175° C.

Example 94

(4-Amino-3-methoxyphenyl)(1-methoxy-2-methylindolizin-3-yl)methanone 700 mg of 10% Pd/C are added to 6 g (0.0176 mol) of (1-methoxy-2-methyl-3-indolizinyl)(3-methoxy-4-nitrophenyl)methanone, a compound of Example 1, in 100 ml of ethanol, followed by 35.71 ml (0.352 mol) of cyclohexene, and the medium is heated under reflux for 2 hours. The reaction medium is cooled, filtered over talc and the catalyst is washed with dichloromethane. The filtrate is concentrated under reduced pressure. The residue is taken up in dichloromethane. The organic phase is washed with 1 N sodium hydroxide and then with water, dried over sodium sulphate and concentrated under reduced pressure. 5.05 g of a yellow powder are recovered.

The product is salified by dissolving the powder obtained above in 60 ml of dichloromethane plus 20 ml of methanol, and then adding 21 ml of 1 N hydrochloric acid in ethyl ether. After adding ethyl ether, the precipitate obtained is filtered off, washed with ethyl ether and then dried. 5.4 g of a yellow powder in hydrochloride form are recovered.

Yield: 88% Melting point: 198° C.

Examples 95 to 117

By carrying out the procedure according to the preparation described above, the compounds described in Table VII below are synthesized by reducing the nitro functional group of the compounds of formula Ia with cyclohexene in the presence of 10% Pd/C as catalyst.

oxy-4-nitrophenyl)methanone in 5 ml of methanol and 10 ml of dichloromethane, followed by 253 µl (5.21 mmol) of hydrazine hydrate, and the medium is stirred at room temperature overnight. The reaction medium is filtered on talc and the catalyst is washed with methanol.

The filtrate is concentrated under reduced pressure. The residue is taken up in ethyl acetate, the organic phase is washed with a saturated aqueous sodium chloride solution, dried over sodium sulphate and concentrated under reduced pressure. 460 mg of a yellow powder are recovered.

The product is salified by dissolving the powder obtained above in a mixture of ethyl acetate and methanol, and then 1.25 ml (1.2 equivalents) of 1 N hydrochloric acid in ethyl ether are added. After addition of ethyl ether, the precipitate obtained is filtered, washed with ethyl ether and then dried. 440 mg of a yellow powder are recovered in the form of the hydrochloride $0.65H_2O$.

Yield: 90% Melting point: 177° C.

TABLE VII

| Example | $R_1$ | $R_2$ | $R_3$ | $R_4$ | Yield (%) | Salts | Melting point or mass spectro. (MH+) |
|---|---|---|---|---|---|---|---|
| 95 | OMe | $C_6H_5$ | OMe | $NH_2$ | 90 | HCl, $0.45H_2O$ | 209° C. |
| 96 | OMe | cPr | OMe | $NH_2$ | 95 | HCl, $0.15H_2O$ | 191° C. |
| 97 | $CO_2Et$ | Me | OMe | $NH_2$ | 91 | HCl | 194° C. |
| 98 | $OCH_2CO_2Et$ | Me | OMe | $NH_2$ | 99 | HCl | 182° C. |
| 99 | $OCH_2CONH_2$ | Me | OMe | $NH_2$ | 87 | HCl | $MH^+ = 354.1$ |
| 100 | $O(CH_2)_2OH$ | Me | OMe | $NH_2$ | 89 | HCl, $0.5H_2O$ | 205° C. |
| 101 | OMe | Me | H | $NH_2$ | 86 | HCl, $0.2H_2O$ | 221° C. |
| 102 | CONHEt | Me | OMe | $NH_2$ | 72 | HCl, $0.45H_2O$ | 221° C. |
| 103 | $CONHCH_2CO_2Et$ | Me | OMe | $NH_2$ | 91 | HCl, $1.05H_2O$ | 196° C. |
| 104 | OMe | Me | $CO_2Me$ | $NH_2$ | 87 | $0.4H_2O$ | 297° C. |
| 105 | $CO_2Et$ | Me | $CO_2Me$ | $NH_2$ | 95 | — | 172° C. |
| 106 | OMe | Me | $NH_2$ | OMe | 82 | HCl | 209° C. |
| 107 | $CO_2Et$ | $C_6H_5$ | OMe | $NH_2$ | 86 | — | 180° C. |
| 108 | $CO_2Et$ | Me | $NH_2$ | OMe | 85 | — | 162° C. |
| 109 | $CO_2Et$ | $CF_3$ | OMe | $NH_2$ | 81 | — | 75° C. |
| 110 | $CO_2Et$ | H | OMe | $NH_2$ | 89 | — | 143° C. |
| 111 | NHCOPh-4-$CO_2Me$ | Me | OMe | $NH_2$ | 72 | HCl | 275° C. |
| 112 | NHCOPh-3-OMe | Me | OMe | $NH_2$ | 77 | HCl, $0.4H_2O$ | 209° C. |
| 113 | NHCOPh(3-OMe)4-$NH_2$ | Me | OMe | $NH_2$ | 82 | 2HCl, $1H_2O$ | 178° C. |
| 114 | NHAc | Me | OMe | $NH_2$ | 57 | HCl, $0.35H_2O$ | 253° C. |
| 115 | N(Me)COPh-3-OMe | Me | OMe | $NH_2$ | 98 | HCl | 113° C. |
| 116 | N(Me)COPh-3-OMe | Me | $CO_2Me$ | $NH_2$ | 99 | — | 91° C. |
| 117 | N(BOC)COPh-3-OMe | Me | $CO_2Me$ | $NH_2$ | 98 | — | 82° C. |

Example 118

(4-Amino-3-methoxyphenyl){1-[(2-chlorobenzyl)oxy]-2-methylindolizin-3-yl}methanone hydrochloride 47 mg of 10% Pd/C are added to 470 mg (1.04 mmol) of {1-[(2-chlorobenzyl)oxy]-2-methylindolizin-3-yl}(3-meth- Examples 119 to 140

By carrying out the procedure according to the preparation described in Example 118, the compounds described in Table VIII below are synthesized by reducing the nitro functional group of the compounds of formula Ia with hydrazine hydrate in the presence of 10% Pd/C as catalyst.

TABLE VIII

| Example | A | $R_1$ | $R_2$ | $R_3$ | $R_4$ | Yield (%) | Salts | Melting point or mass spectro. (MH+) |
|---|---|---|---|---|---|---|---|---|
| 119 | CO | OBn | $C_6H_5$ | OMe | $NH_2$ | 94 | HCl, $0.2H_2O$ | 207° C. |
| 120 | CO | $O(CH_2)_2NMe_2$ | Me | OMe | $NH_2$ | 31 | 2HCl, $2H_2O$ | 246° C. |
| 121 | CO | OBn-4-Cl | Me | OMe | $NH_2$ | 99 | HCl | 177° C. |
| 122 | CO | OBn-3-OMe | Me | OMe | $NH_2$ | 95 | HCl | 181° C. |

TABLE VIII-continued

| Example | A | $R_1$ | $R_2$ | $R_3$ | $R_4$ | Yield (%) | Salts | Melting point or mass spectro. (MH+) |
|---|---|---|---|---|---|---|---|---|
| 123 | CO | OBn-4-OMe | Me | OMe | $NH_2$ | 99 | HCl, $0.3H_2O$ | 128° C. |
| 124 | CO | OBn-2-OMe | Me | OMe | $NH_2$ | 99 | HCl | 164° C. |
| 125 | CO | OBn-3-$CO_2$Me | Me | OMe | $NH_2$ | 75 | HCl | 185° C. |
| 126 | CO | OBn-4-$CO_2$Me | Me | OMe | $NH_2$ | 93 | HCl, $1H_2O$ | 160° C. |
| 127 | CO | OBn-3-Cl | Me | OMe | $NH_2$ | 96 | HCl | 175° C. |
| 128 | CO | N(Me)Bn | Me | OMe | $NH_2$ | 78 | HCl, $1.6H_2O$ | 114° C. |
| 129 | CO | NHBOC | Me | OMe | $NH_2$ | 95 | base | $MH^+ = 396.4$ |
| 130 | CO | NHMe | Me | OMe | $NH_2$ | 88 | HCl, $1.15H_2O$ | 210° C. |
| 131 | CO | $NHSO_2$Me | Me | OMe | $NH_2$ | 83 | HCl | 228° C. |
| 132 | CO | OMe | Me | $NH_2$ | $CO_2$Me | 72 | — | 135° C. |
| 133 | $SO_2$ | OMe | Me | H | $NH_2$ | 66 | — | 157° C. |
| 134 | $SO_2$ | OMe | Me | $NH_2$ | H | 45 | — | 137° C. |
| 135 | CO | $OCH_2$cPr | Me | OMe | $NH_2$ | 99 | HCl | 181° C. |
| 136 | CO | OiBu | Me | OMe | $NH_2$ | 60 | HCl | 103° C. |
| 137 | CO | $NMe_2$ | Me | OMe | $NH_2$ | 80 | 2HCl, $0.2H_2O$ | 171° C. |
| 138 | CO | OBn-2-$CO_2$Et | Me | OMe | $NH_2$ | 98 | HCl, $0.5H_2O$ | 185° C. |
| 139 | CO | NHBn-3-OMe | Me | OMe | $NH_2$ | 72 | HCl | 186° C. |
| 140 | CO | N(Me)Bn-3-OMe | Me | OMe | $NH_2$ | 95 | HCl, $1.5H_2O$ | 161° C. |

Example 141

4-Chloro-N-[3-(4-amino-3-methoxybenzoyl)-2-methylindolizin-1-yl]benzamide

A mixture of 384 mg (0.83 mmol) of 4-chloro-N-[3-(3-methoxy-4-nitrobenzoyl)-2-methylindolizin-1-yl]benzamide and 115 mg of platinum oxide in 9 ml of dimethylformamide is stirred, under 5 bar of hydrogen, at room temperature for 24 hours, and then filtered on talc. The filtrate is concentrated under reduced pressure.

The product is purified by chromatography on silica gel, eluting with toluene/acetone (9/1 to 8/2). 1 ml of 1 N hydrochloric acid in ethyl ether is added to the yellow powder obtained, suspended in 5 ml of dichloromethane and 5 ml of methanol. The precipitate obtained is filtered off, washed with acetone and then dissolved in 2 ml of methanol and 40 ml of water. The hydrochloride thus obtained is freeze-dried. 162 mg of an orange-coloured powder are obtained.

Yield: 50% Melting point: 191° C.

Example 142

[1-(2-Hydroxyethoxy)-2-methylindolizin-3-yl](3-methoxy-4-nitrophenyl)methanone 1.52 ml of 1 N sodium hydroxide are added to 420 mg (1.02 mmol) of 2-{[3-(3-methoxy-4-nitrobenzoyl)-2-methylindolizin-1-yl]oxy}ethyl acetate, a compound of Example 79, dissolved in 6 ml of dioxane, and the medium is stirred at room temperature for 6 hours. The reaction medium is poured over water and ethyl acetate. The organic phase is separated after settling out, washed with water, dried over sodium sulphate and concentrated under reduced pressure. 340 mg of an orange-coloured powder are obtained, which powder is used without further purification in the subsequent nitro reduction step.

Yield: 90% Melting point: 142° C.

Example 143

Sodium salt of 4-[(1-methoxy-2-methyl-3-indolizinyl)carbonyl]benzoic acid 2.45 ml of 1 N sodium hydroxide are added to 720 mg (2.23 mmol) of methyl 4-[(1-methoxy-2-methylindolizin-3-yl)carbonyl]benzoate, a compound of Example 8, in solution in 15 ml of methanol plus 15 ml of dioxane, and the medium is stirred at room temperature overnight. The reaction medium is concentrated under reduced pressure. The residue is taken up in water, washed with ethyl ether and separated after settling out. The aqueous phase is acidified with 1 N hydrochloric acid and extracted with dichloromethane.

The organic phase is washed with water, dried over sodium sulphate and concentrated under reduced pressure. 700 mg of an orange-coloured powder are obtained, which powder is suspended in 20 ml of methanol and then one equivalent of 1 N sodium hydroxide is added. The solution obtained is concentrated under reduced pressure. The residue is crystallized from acetone. The product is filtered off, washed with acetone and then with ethyl ether, dried, and 680 mg of a yellow powder are obtained.

Yield (Na salt): 92% Melting point >400° C.

Examples 144 to 157

By carrying out the procedure according to the method described in Example 143, the compounds described in Table IX below are synthesized by saponification of the ester functional group of the compounds of formula Id.

TABLE IX

| Example | $R_1$ | $R_2$ | $R_3$ | $R_4$ | Yield (%) | Salts | Melting point |
|---|---|---|---|---|---|---|---|
| 144 | OMe | Me | $CO_2H$ | H | 76 | Na | 218° C. |
| 145 | OMe | Me | $NO_2$ | $CO_2H$ | 85 | Na | 265° C. |
| 146 | OMe | Me | $NH_2$ | $CO_2H$ | 77 | Na | 315° C. |
| 147 | OBn-3-OMe | Me | H | $CO_2H$ | 81 | Na, $0.7H_2O$ | 268° C. |
| 148 | OMe | Me | OMe | $CO_2H$ | 87 | Na, $1H_2O$ | 235° C. |
| 149 | OMe | Me | H | $CH_2CO_2H$ | 91 | Na, $0.7H_2O$ | 248° C. |
| 150 | OMe | Me | $CO_2H$ | $NH_2$ | 98 | Na, $1H_2O$ | 258° C. |
| 151 | OMe | Me | $CO_2H$ | $NO_2$ | 83 | Na, $0.95H_2O$ | 164° C. |
| 152 | OMe | Me | $CO_2H$ | OMe | 92 | Na, $0.65H_2O$ | 318° C. |
| 153 | H | Me | $CO_2H$ | $NH_2$ | 95 | Na, $1.3H_2O$ | 300° C. |
| 154 | OMe | cPr | $CO_2H$ | $NH_2$ | 100 | Na, $1.75H_2O$ | 249° C. |
| 155 | N(Me)COPh-3-OMe | Me | $CO_2H$ | $NH_2$ | 77 | Na, $3.2H_2O$ | 230° C. |
| 156 | NHBn-3-OMe | Me | $CO_2H$ | $NH_2$ | 83 | Na, $1.15H_2O$ | 164° C. |
| 157 | N(Me)Bn-3-OMe | Me | $CO_2H$ | $NH_2$ | 78 | Na, $1.2H_2O$ | 211° C. |

Example 158

2-Amino-5-({1-[3-methoxybenzoyl)amino]-2-methylindolizin-3-yl}carbonyl)benzoic acid 6.6 ml of a sodium hydroxide solution (2 N) are added to 3.31 g (6.0 mmol) of methyl 5-({1-[(3-methoxybenzoyl)amino]-2-methylindolizin-3-yl}carbonyl)-2-[2,2,2-trifluoroacetyl)amino]benzoate in suspension in 40 ml of dioxane and 20 ml of methanol. The reaction medium is heated under reflux for 2.5 hours, and then it is allowed to return to room temperature and concentrated under reduced pressure. The residue obtained is taken up in a saturated aqueous sodium bicarbonate solution and extracted with ethyl acetate. After decantation, the aqueous phase is acidified with a molar hydrochloric acid solution. The precipitate obtained is filtered off, thoroughly washed with water and dried under vacuum. 2.4 g of a yellow powder are obtained.

Yield: 90% Melting point: 290° C.

Na salt, monohydrate: melting point: 265° C.

Examples 159 to 174

By carrying out the procedure according to the method described above, the compounds of formula I, in which A represents —CO— and which are described in Table X below, are synthesized by hydrolysing the methyl ester and the trifluoroacetamide of $R_3$ and $R_4$ with sodium hydroxide.

TABLE X

| Example | $R_1$ | $R_2$ | $R_3$ | $R_4$ | Yield (%) | Salts | Melting Point (° C.) |
|---|---|---|---|---|---|---|---|
| 159 | NHCOPh-2,3-OMe | Me | $CO_2H$ | $NH_2$ | 75 | Na, $3.0 H_2O$ | 236 |
| 160 | NHCOPh-2,3-OMe | Me | $CO_2H$ | $NH_2$ | 77 | Na, $2.5 H_2O$ | 265 |
| 161 | NHCOPh-3,4-OMe | Me | $CO_2H$ | $NH_2$ | 79 | Na, $2.0 H_2O$ | 331 |
| 162 | NHCOPh-3,4,5-OMe | Me | $CO_2H$ | $NH_2$ | 92 | Na, $1.5 H_2O$ | 349 |
| 163 | NHCOPh-3,5-OMe | Me | $CO_2H$ | $NH_2$ | 71 | Na, $2.0 H_2O$ | 293 |
| 164 | NHCOPh-(3-OMe)4-Me | Me | $CO_2H$ | $NH_2$ | 78 | Na, $1.0 H_2O$ | 277 |
| 165 | NHCOPh-3,4-methylenedioxy | Me | $CO_2H$ | $NH_2$ | 94 | Na, $1.8 H_2O$ | 400 |
| 166 | NHCOPh(4-Cl)-3-OMe | Me | $CO_2H$ | $NH_2$ | 67 | Na, $3.0 H_2O$ | 320 |
| 167 | NHCOPh(4-F)3-OMe | Me | $CO_2H$ | $NH_2$ | 72 | Na, $2.25 H_2O$ | 276 |
| 168 | NHCOPh(4-Cl)2.5-OMe | Me | $CO_2H$ | $NH_2$ | 82 | Na, $2.5 H_2O$ | 280 |
| 169 | NHCOPh-5-indoyl | Me | $CO_2H$ | $NH_2$ | 86 | Na, $2.8 H_2O$ | 296 |
| 170 | NHCOPh(3-OMe)4-$CO_2H$ | Me | $CO_2H$ | $NH_2$ | 74 | 2Na, $2.5 H_2O$ | 323 |
| 171 | NHCOPh-3-$OCF_3$ | Me | $CO_2H$ | $NH_2$ | 76 | Na, $1.5 H_2O$ | 321 |
| 172 | NHCOPh-2,4,5-OMe | Me | $CO_2H$ | $NH_2$ | 53 | Na, $2.5 H_2O$ | 272 |
| 173 | $NHSO_2$Ph-3-OMe | Me | $CO_2H$ | $NH_2$ | 50 | Na, $2 H_2O$ | 238 |
| 174 | NHCONHPh-3-OMe | Me | $CO_2H$ | $NH_2$ | 75 | Na, $1.2 H_2O$ | 378 |

Example 175

3-(4-Amino-3-methoxybenzoyl)-2-methylindolizin-1-ylcarboxylic acid 30 ml of 2 N sodium hydroxide are added to 2.1 g (5.96 mmol) of ethyl 3-(4-amino-3-methoxybenzoyl)-2-methyl-1-indolizinecarboxylate in solution in 30 ml of dioxane, and the medium is heated under reflux for 20 hours. The reaction medium is concentrated under reduced pressure.

The residue is taken up in water, washed with ethyl ether and separated after settling out. The aqueous phase is acidified to pH 6.5 with a 10% aqueous potassium hydrogen sulphate solution and extracted with ethyl acetate. The organic phase is washed with water, dried over sodium sulphate and concentrated under reduced pressure. 1.8 g of a yellow powder are obtained.

Yield: 93%

Two salts of the compound are then prepared: Sodium salt, monohydrate, melting point: 224° C.; hydrochloride, melting point: 213° C.

Examples 176 to 185

By carrying out the procedure according to the preparation described above, the compounds described in Table XI below are synthesized by saponification of the ester functional group contained in the substituent $R_1$ of the compounds of formula Id, in which A represents a radical —CO—, with sodium hydroxide.

TABLE XI

| Example | $R_1$ | $R_2$ | $R_3$ | $R_4$ | Yield (%) | Salts | Melting point (° C.) |
|---|---|---|---|---|---|---|---|
| 176 | $OCH_2CO_2H$ | Me | 3-OMe | 4-$NH_2$ | 91 | — | 227° C. |
| 177 | $CONHCH_2CO_2H$ | Me | 3-OMe | 4-$NH_2$ | 90 | Na, 0.95$H_2O$ | 297° C. |
| 178 | OBn-3-$CO_2H$ | Me | 3-OMe | 4-$NH_2$ | 84 | Na, 1.25$H_2O$ | 207° C. |
| 179 | OBn-4-$CO_2H$ | Me | 3-OMe | 4-$NH_2$ | 76 | Na, 0.7$H_2O$ | 216° C. |
| 180 | $CO_2H$ | $C_6H_5$ | 3-OMe | 4-$NH_2$ | 84 | Na, 1.25$H_2O$ | 305° C. |
| 181 | OBn-2-$CO_2H$ | Me | 3-OMe | 4-$NH_2$ | 100 | Na, 1.5$H_2O$ | Dec.174 |
| 182 | $CO_2H$ | $CF_3$ | 3-OMe | 4-$NH_2$ | 87 | Na, 1$H_2O$ | 330° C. |
| 183 | $CO_2H$ | H | 3-OMe | 4-$NH_2$ | 90 | Na, 1.9$H_2O$ | 254° C. |
| 184 | $CO_2H$ | Me | 3-$NH_2$ | 4-OMe | 91 | Na, 1$H_2O$ | 225° C. |
| 185 | NHCOPh-4-$CO_2H$ | Me | OMe | $NH_2$ | 48 | HCl | 256° C. |

TABLE XII

| Example | $R_1$ | $R_2$ | $R_3$ | $R_4$ | Yield (%) | Salts | Melting point (° C.) |
|---|---|---|---|---|---|---|---|
| 187 | $OCH_2CO_2H$ | Me | H | $CO_2H$ | 90 | 2Na, 2$H_2O$ | >400° C. |
| 188 | $CO_2H$ | Me | OMe | $CO_2H$ | 96 | 2Na, 1.5$H_2O$ | 323° C. |
| 189 | $CO_2H$ | Me | $CO_2H$ | $NH_2$ | 82 | 2Na, 1.9$H_2O$ | 336° C. |
| 190 | $CO_2H$ | Me | $CO_2H$ | $NO_2$ | 96 | 2Na, 2.5$H_2O$ | 321° C. |
| 191 | $CO_2H$ | Me | $CO_2H$ | OMe | 66 | 2Na, 1.4$H_2O$ | 310° C. |

Example 186

Disodium salt of 3-(4-carboxybenzoyl)-2-methylindolizin-1-ylcarboxylic acid 7.47 ml of 1 N sodium hydroxide are added to 910 mg (2.49 mmol) of ethyl 3-[4-(methoxycarbonyl)benzoyl]-2-methylindolizin-1-ylcarboxylate in solution in 20 ml of dioxane plus 20 ml of ethanol, and the medium is heated under reflux for 6 hours. The reaction medium is concentrated under reduced pressure. The residue is taken up in water, washed with ethyl ether and separated after settling out. The aqueous phase is acidified with 1 N hydrochloric acid and extracted with ethyl acetate. The organic phase is washed with water, dried over sodium sulphate and concentrated under reduced pressure. 650 mg of a yellow powder are obtained, which powder is suspended in 20 ml of methanol, and then 4.02 ml of 1 N sodium hydroxide (2 eq.) are added.

The solution obtained is concentrated under reduced pressure. The residue is crystallized from acetone. The product is filtered off, washed with acetone and then with ethyl ether and dried. 700 mg of a yellow powder are obtained.

Yield, disodium salt, dihydrate: 81% Melting point: >400° C.

Examples 187 to 191

By carrying out the procedure according to Example 186, the compounds described in Table XII below are synthesized by saponification of the ester functional groups contained in the substituents $R_1$ and $R_4$ of the compounds of formula I, in which A represents a radical —CO—, with 1 N sodium hydroxide.

Example 192

(4-{[3-(Dibutylamino)propyl]amino}-3-methoxyphenyl)(1-methoxy-2-methylindolizin-3-yl)methanone hydrochloride 700 mg (2.25 mmol) of (4-amino-3-methoxyphenyl)(1-methoxy-2-methylindolizin-3-yl)methanone, a compound described in Example 94, dissolved in 5 ml of tetrahydrofuran, are added to 278.4 mg (2.25 mmol) of potassium tert-butoxide in 5 ml of tetrahydrofuran, and the medium is stirred for 15 minutes at room temperature.

510.5 mg (2.48 mmol) of dibutylaminopropyl chloride in 5 ml of tetrahydrofuran are then added, and the medium is heated under reflux overnight.

The reaction medium is cooled and poured over water and then extracted with ethyl acetate. The organic phase is separated after settling out, washed with water, dried over sodium sulphate and concentrated under reduced pressure.

The product is purified by chromatography on a silica column, eluting with a dichloromethane/acetone (9/1) and then (1/1) mixture.

700 mg of an orange-coloured resin are obtained, which resin is salified in ethyl ether by adding one equivalent of 1 N hydrochloric acid in ethyl ether.

The crystals obtained are filtered off, washed with ethyl ether and dried. An orange-coloured powder is obtained in the form of the hydrochloride, 1.25$H_2O$.

Yield: 65% Melting point: 51° C.

Example 193

[3-Methoxy-4-(methylamino)phenyl](1-methoxy-2-methylindolizin-3-yl)methanone hydrochloride This compound is obtained according to the same procedure as that described in Example 192, by alkylating (4-amino-3-methoxyphenyl)(1-methoxy-2-methylindolizin-3-yl)methanone with methyl iodide. A yellow powder is obtained.

Yield: 45% Melting point: 172° C.

Example 194

(4-{[3-(Dibutylamino)propyl]amino}-3-methoxyphenyl)(1-methoxy-2-phenylindolizin-3-yl)methanone dihydrochloride Obtained according to the same procedure as that described in Example 192, by alkylating (4-amino-3-methoxyphenyl)(1-methoxy-2-phenylindolizin-3-yl)methanone, a compound of Example 95, with dibutylaminopropyl chloride. An orange-coloured powder is obtained (dihydrochloride: $1.3H_2O$).

Yield: 37% Melting point: 158° C.

Example 195

Ethyl 2-{2-methoxy-4-[(1-methoxy-2-methylindolizin-3-yl)carbonyl]anilino}acetate This compound was obtained according to the same procedure as that described in Example 192, by alkylating (4-amino-3-methoxyphenyl)(1-methoxy-2-methylindolizin-3-yl)methanone, a compound of Example 94, with ethyl bromoacetate. A yellow powder is obtained.

Yield: 60.5% Melting point: 125° C.

Example 196

2-{2-Methoxy-4-[(1-methoxy-2-methylindolizin-3-yl)carbonyl]anilino}acetic acid 3.15 ml of 1 N sodium hydroxide are added to 1 g (2.52 mmol) of ethyl 2-{2-methoxy-4-[(1-methoxy-2-methylindolizin-3-yl)carbonyl]anilino}acetate, a compound obtained in Example 195, in solution in 10 ml of ethanol, and the medium is stirred at room temperature overnight. The reaction medium is concentrated under reduced pressure. The residue is taken up in water, washed with ethyl ether and separated after settling out. The aqueous phase is neutralized with 1 N hydrochloric acid. The precipitate formed is filtered off, washed with water, dried and then taken up in ethyl ether, filtered and dried. A yellow powder is obtained.

Yield: 48.5% Melting point: 196° C.

Example 197

Ethyl 2-{2-methoxy-4-[(1-methoxy-2-phenylindolizin-3-yl)carbonyl]anilino}acetate This compound was obtained according to the method described in Example 192, by alkylating (4-amino-3-methoxyphenyl)(1-methoxy-2-phenylindolizin-3-yl)methanone, a compound of Example 95, with ethyl bromoacetate. A yellow powder is obtained.

Yield: 78% Melting point: 132° C.

Example 198

2-{2-Methoxy-4-[(1-methoxy-2-phenylindolizin-3-yl)carbonyl]anilino}acetic acid

Obtained according to the same procedure as the compound of Example 196, by saponification of ethyl 2-{2-methoxy-4-[(1-methoxy-2-phenylindolizin-3-yl)carbonyl]anilino}acetate, a compound of Example 197, with 1 N sodium hydroxide. A yellow powder is obtained.

Yield: 80% Melting point: 206° C.

Example 199

3-(Dibutylamino)-N-{2-methoxy-4-[(1-methoxy-2-methylindolizin-3-yl)carbonyl]phenyl}propanamide hydrochloride 2.5 ml (17.7 mmol) of triethylamine are added to 2.5 g (8.06 mmol) of (4-amino-3-methoxyphenyl)(1-methoxy-2-methylindolizin-3-yl)methanone, a compound of Example 94, in 20 ml of dichloromethane cooled to 5° C., followed by 846 µl (8.86 mmol) of 3-chloropropionyl chloride in solution in 10 ml of dichloromethane, and the medium is stirred for 3 hours at room temperature. The reaction medium is washed with water and then with saturated aqueous sodium chloride solution, dried over sodium sulphate and concentrated under reduced pressure.

The residue obtained is dissolved in 40 ml of ethanol and 1.7 g (13.2 mmol) of dibutylamine are added, and then the medium is heated under reflux for 7 hours. The reaction medium is concentrated under reduced pressure. The product is purified by chromatography on a silica column, eluting with a dichloromethane/methanol (98:2) mixture. 2.6 g of product are obtained, which product is salified by adding 1 N hydrochloric acid in ethyl ether. A yellow powder is obtained (hydrochloride, $0.25H_2O$).

Yield: 65% Melting point: 82° C.

Example 200

3-(Dibutylamino)-N-{2-methoxy-4-[(1-methoxy-2-phenylindolizin-3-yl)carbonyl]phenyl}propanamide hydrochloride This compound was obtained according to the same procedure as that described in Example 199, by acylation of (4-amino-3-methoxyphenyl)(1-methoxy-2-phenylindolizin-3-yl)methanone with 3-chloropropionyl chloride, followed by amination with dibutylamine. A yellow powder is obtained (hydrochloride, hemihydrate), Yield: 52% Melting point: 190° C.

Example 201

N-{2-Methoxy-4-[(1-methoxy-2-methylindolizin-3-yl)carbonyl]phenyl}acetamide

This compound was obtained according to the same procedure as that described in Example 199, by acylation of (4-amino-3-methoxyphenyl)(1-methoxy-2-methylindolizin-3-yl)methanone, a compound of Example 94, with acetyl chloride. The product is purified by flash chromatography on silica, eluting with a dichloromethane/methanol (99:1) mixture. A yellow powder is obtained ($0.3H_2O$).

Yield: 73% Melting point: 180° C.

Example 202

Ethyl 2-methoxy-4-[(1-methoxy-2-methylindolizin-3-yl)carbonyl]phenylcarbamate

This compound was obtained according to the same procedure as that described in Example 199 by acylation of (4-amino-3-methoxyphenyl)(1-methoxy-2-methylindolizin-3-yl)methanone with ethyl chloroformate. The product is purified by flash chromatography on silica, eluting with dichloromethane. A yellow powder is obtained.

Yield: 41% Melting point: 140° C.

Example 203

Ethyl 2-{[3-(dibutylamino)propanoyl]-2-methoxy-4-[(1-methoxy-2-methylindolizin-3-yl)carbonyl]anilino}acetate hydrochloride 1 g (2.03 mmol) of 3-(dibutylamino-N-{2-methoxy-4-[(1-methoxy-2-methylindolizin-3-yl)carbonyl]phenyl}propanamide, a compound of Example 199, in solution in 10 ml of dimethylformamide, is added dropwise to 89.1 mg (2.23 mmol) of sodium hydride, at 60% as a dispersion in oil, in 10 ml of dimethylformamide, and then the medium is stirred at room temperature for 1 hour. 247 µl (2.23 mmol) of ethyl bromoacetate are then added, and the medium is stirred at room temperature overnight.

The reaction medium is poured over water and ethyl acetate. The organic phase is separated after settling out, washed with water, dried over sodium sulphate and concentrated under reduced pressure. The product is purified by flash chromatography on a silica column, eluting with a dichloromethane/methanol (97:3) mixture. 850 mg of an oil are obtained, which oil is dissolved in ethyl ether and salified by adding one equivalent of 1 N hydrochloric acid in ethyl ether. Yellow crystals are obtained (hydrochloride, hydrate).

Yield: 72% Melting point: 67° C.

Example 204

Hydrochloride of 2-{[3-(dibutylamino)propanoyl]-2-methoxy-4-[(1-methoxy-2-methylindolizin-3-yl)carbonyl]anilino}acetic acid 586 µl of 1 N sodium hydroxide are added to 340 mg (0.586 mmol) of ethyl 2-{[3-(dibutylamino)propanoyl]-2-methoxy-4-[(1-methoxy-2-methylindolizin-3-yl)carbonyl]anilino}acetate obtained in Example 203, in solution in 5 ml of ethanol, and the medium is stirred at room temperature overnight. The reaction medium is concentrated under reduced pressure. The residue is taken up in water, washed with ethyl ether and separated after settling out. The aqueous phase is neutralized with 1 N hydrochloric acid, and extracted with dichloromethane. The organic phase is dried over sodium sulphate and concentrated under reduced pressure.

The product is purified by flash chromatography on a silica column, eluting with a dichloromethane/methanol (8:2) mixture. 230 mg of an oil are obtained, which oil is dissolved in ethyl acetate and salified by adding one equivalent of 1 N hydrochloric acid in ethyl ether. A yellow powder is obtained (hydrochloride, 0.6H$_2$O).

Yield: 71% Melting point: 151° C.

Example 205

Ethyl 2-{[3-(dibutylamino)propanoyl]-2-methoxy-4-[(1-methoxy-2-phenyl-3-indolizinyl)carbonyl]anilino}acetate hydrochloride Obtained according to the method described in Example 203, by alkylating 3-(dibutylamino)-N-{2-methoxy-4-[(1-methoxy-2-phenylindolizin-3-yl)carbonyl]phenyl}propanamide, a compound of Example 200, with ethyl bromoacetate. A yellow powder (hydrochloride) is obtained after salification with 1 N hydrochloric acid in ethyl ether.

Yield: 55% Melting point: 64° C.

Example 206

Hydrochloride of 2-{[3-(dibutylamino)propanoyl]-2-methoxy-4-[(1-methoxy-2-phenylindolizin-3-yl)carbonyl]anilino}acetic acid Obtained according to the same procedure as that of Example 204, by saponification of ethyl 2-{[3-(dibutylamino)propanoyl]-2-methoxy-4-[(1-methoxy-2-phenylindolizin-3-yl)carbonyl]anilino}acetate, a compound of Example 205, with 1 N sodium hydroxide. A yellow powder is obtained after salification with 1 N hydrochloric acid in ethyl ether.

Yield: 75% Melting point: 113° C.

Example 207

2-(Dibutylamino)-N-{2-methoxy-4-[(1-methoxy-2-methylindolizin-3-yl)carbonyl]phenyl}-1-ethanesulphonamide hydrochloride 471.5 µl (3.38 mmol) of triethylamine are added to 1 g (3.22 mmol) of (4-amino-3-methoxyphenyl)(1-methoxy-2-methylindolizin-3-yl)methanone in 15 ml of dichloromethane, followed by 346.9 µl (3.22 mmol) of 2-chloroethylsulphonyl chloride in solution in 5 ml of dichloromethane, and the medium is stirred at room temperature overnight. The reaction medium is washed with water and then with a saturated aqueous sodium chloride solution, dried over sodium sulphate and concentrated under reduced pressure.

The residue obtained is dissolved in 10 ml of ethanol. 375 mg (2.9 mmol) of dibutylamine are added and the medium is heated under reflux for 4 hours. The reaction medium is concentrated under reduced pressure. The product is purified by chromatography on a silica column, eluting with a dichloromethane/methanol (98:2) mixture. 1.18 g of product are obtained, which product is salified by adding 1 N hydrochloric acid in ethyl ether. A yellow powder is obtained (hydrochloride, hemihydrate).

Yield: 69% Melting point: 91° C.

Example 208

2-(Dibutylamino)-N-{2-methoxy-4-[(1-methoxy-2-phenylindolizin-3-yl)carbonyl]phenyl}-1-ethanesulphonamide hydrochloride This compound is obtained according to the same procedure as the compound of Example 207, by sulphonylation of (4-amino-3-methoxyphenyl)(1-methoxy-2-phenylindolizin-3-yl)methanone with 2-chloroethylsulphonyl chloride, followed by amination with dibutylamine. A yellow powder is obtained (hydrochloride, hemihydrate).

Yield: 63% Melting point: 111° C.

Example 209

N-{2-Methoxy-4-[(1-methoxy-2-methylindolizin-3-yl)carbonyl]phenyl}methanesulphonamide Obtained according to the same procedure as the compound of Example 207, by sulphonylation of (4-amino-3-methoxyphenyl)(1-methoxy-2-methylindolizin-3-yl)methanone with methanesulphonyl chloride. The product is purified by chromatography on a silica column, eluting with a toluene/ethyl acetate (7:3) mixture. A yellow powder is obtained.
Yield: 67% Melting point: 165° C.

Example 210

Ethyl 3-{3-methoxy-4-[(methylsulphonyl)amino]benzoyl}-2-methylindolizin-1-ylcarboxylate This compound was obtained according to the same procedure as that described in Example 207, by sulphonylation of ethyl 3-(4-amino-3-methoxybenzoyl)-2-methylindolizin-1-ylcarboxylate, a compound of Example 97, with methanesulphonyl chloride. The product is purified by chromatography on a silica column, eluting with a toluene/ethyl acetate (8:2) mixture. A yellow powder is obtained.
Yield: 57% Melting point: 178° C.

Example 211

Sodium salt of 3-{3-methoxy-4-[(methylsulphonyl)amino]benzoyl}-2-methylindolizin-1-ylcarboxylic acid 1 ml of caustic soda is added to 290 mg (0.675 mmol) of ethyl 3-{3-methoxy-4-[(methylsulphonyl)amino]benzoyl}-2-methylindoliz-1-ylcarboxylate in 7 ml of dioxane plus 7 ml of water, and the medium is heated under reflux for 6 hours.
The medium is cooled, poured over water and neutralized with an aqueous potassium hydrogen sulphate solution, and then extracted with ethyl acetate. The organic phase is washed with water, dried over sodium sulphate and concentrated under reduced pressure.
220 mg of a yellow powder are obtained. The product is salified by adding one equivalent of 1 N sodium hydroxide to a suspension of the product in water and stirring at room temperature until dissolution is obtained.
The solution obtained is then freeze-dried. A yellow freeze-dried product is recovered (Na salt, 1.85H$_2$O).
Yield: 81% Mass spectrometry (ES+ mode) MH$^+$=403.2

Example 212

Hydrochloride of 2-{{[2-(dibutylamino)ethyl]sulphonyl}-2-methoxy-4-[(1-methoxy-2-methylindolizin-3-yl)carbonyl]anilino}acetic acid Step A Benzyl 2-{{[2-(dibutylamino)ethyl]sulphonyl}-2-methoxy-4-[(1-methoxy-2-methylindolizin-3-yl)carbonyl]anilino}acetate 125 mg (0.906 mmol) of potassium carbonate are added to 400 mg (0.755 mmol) of 2-(dibutylamino)-N-{2-methoxy-4-[(1-methoxy-2-methylindolizin-3-yl)carbonyl]phenyl}-1-ethanesulphonamide, a compound of Example 207, in solution in 10 ml of dimethylformamide, followed by 142 μl (0.906 mmol) of benzyl bromoacetate, and the medium is heated at 60° C. for 1 hour. The reaction medium is poured over water and ethyl acetate.
The organic phase is separated after settling out, washed with water, dried over sodium sulphate and concentrated under reduced pressure.
The product is purified by flash chromatography on a silica column, eluting with a dichloromethane/methanol (98:2) mixture. 440 mg of an oil are obtained, which oil is used directly in the next step.
Yield: 86%

Step B 1.3 ml (12.7 mmol) of cyclohexene are added to 430 mg (0.634 mmol) of benzyl 2-{{[2-(dibutylamino)ethyl]sulphonyl}-2-methoxy-4-[(1-methoxy-2-methylindolizin-3-yl)carbonyl]anilino}acetate in 5 ml of ethanol, in the presence of 100 mg of 10% Pd/C, and the medium is heated under reflux for 3 hours. The reaction medium is cooled. The catalyst is filtered off and the filtrate is concentrated under reduced pressure.
The product is purified by flash chromatography on a silica column, eluting with a dichloromethane/methanol (9:1) mixture. 250 mg of an oil are obtained, which oil is dissolved in ethyl acetate and salified by adding one equivalent of 1 N hydrochloric acid in ethyl ether. An orange-coloured powder is obtained (hydrochloride, dihydrate).
Yield: 67% Melting point: 85° C.

Example 213

Benzyl 2-{{[2-(dibutylamino)ethyl]sulphonyl}-2-methoxy-4-[(1-methoxy-2-phenylindolizin-3-yl)carbonyl]anilino}acetate hydrochloride This compound was obtained according to the same procedure as Example 212, Step A, by alkylating 2-(dibutylamino)-N-{2-methoxy-4-[(1-methoxy-2-methylindolizin-3-yl)carbonyl]phenyl}-1-ethanesulphonamide, with benzyl bromoacetate.
A yellow powder (hydrochloride, hemihydrate) is obtained after salification with 1 N hydrochloric acid in ethyl ether.
Yield: 55% Melting point: 95° C.

Example 214

Hydrochloride of 2-({[2-(dibutylamino)ethyl]sulphonyl}-2-methoxy-4-[(1-methoxy-2-phenylindolizin-3-yl)carbonyl]anilino}acetic acid This compound was obtained according to the same procedure as Example 212, Step B, by hydrogenating benzyl 2-{{[2-(dibutylamino)ethyl]sulphonyl}-2-methoxy-4-[(1-methoxy-2-phenylindolizin-3-yl)carbonyl]anilino}acetate, a compound of Example 213, with cyclohexene in the presence of Pd/C in ethanol. A yellow powder (hydrochloride, 1.5H$_2$O) is obtained after salification with 1 N hydrochloric acid in ethyl ether.
Yield: 75% Melting point: 113° C.

Example 215

Study of the Binding of $^{125}$I-b-FGF to the Purified Receptor FGF R α IIIc by the Proximity Scintillation Method NBS plates (NBS plate 96 well solid white CORNING 3600) are coated with 100 μl of 0.1% gelatine per well, for 2 hours at 37° C. At the end of the incubation, the coating is removed, the plates are rinsed and thoroughly dried. 100 µl of binding buffer (40 mM Bis Tris buffer, pH 7.0) are distributed into the plates.

Dilutions of the compounds of the invention are distributed into the wells in an amount of 10 µl/well. There are then distributed 10 µl/well of b-FGF (AMERSHAM ARM 35050) and 10 µl/well of FGF R α IIIc (R&D Systems 658 FR). Next, there are added 10 µl/well of $^{125}$I-b-FGF (Dupont NEN NEX 268—specific activity>70 µCi) and 50 µl/well of SPA beads (AMERSHAM RPQN 00019). The plate is shaken for a few seconds and it is incubated for 60 minutes at 37° C., protected from light.

At the end of the incubation, the plate is read in a MIBRO-BETA TRILUX radioactivity counter (WALLAC-PERKI-NELMER).

The compounds of the invention demonstrated a specific activity of between $10^{-6}$ M and $10^{-9}$ M.

Example 216

Effects of the Compounds of formula I on the Proliferation of HUVECs Versus 30 ng/ml of b-FGF or 10 ng/ml of a-FGF Coat the 24-well plates (FALCON PRIMARIA) with 200 µl of a solution of fibronectin (50 µg/ml prepared in PBS)/well.

Inoculate in an amount of 30 000 cells/ml/well in an RPMI 1640 medium+10% FCS+1% glutamine+heparin-ECGF (HE) mixture.

Incubate at 37° C., 5% $CO_2$, the time required for the cells to adhere.

Dissolve the products and prepared solutions in DMSO/reaction medium having a final concentration of 1 µM final at $10^{-7}$ M.

After adhesion of the cells for 6 hours at 37° C. in the presence of 5% $CO_2$, the medium is replaced with RPMI 1640 0.1% FSC+glutamine+HE.

For the derivatization, there is used as negative control 0.1% FCS, as positive control 0% FCS and as control 0.1% FCS+30 ng/ml of b-FGF or 10 ng/ml of a-FGF. Incubation is then carried out for 24 hours at 37° C. in the presence of 5% $CO_2$.

The second day, the cells are rinsed with 1 ml PBS and 200 µl of trypsin, and they are then recovered in isotone. Counting is carried out (n>9 µm).

In this test of proliferation of endothelial cells induced by b-FGF or a-FGF, the compounds of the invention demonstrated a specific activity of between $10^{-5}$ M and $10^{-9}$ M.

Example 217

Model of Angiogenesis in vitro

Prepare the gels by distributing into each chamberslide well (Biocoat Cellware rat tail collagen, Type I, 8-well culturesides: Becton Dickinson 354630) 160 µl of matrigel diluted 1/6 (Growth factor reduced Matrigel: Becton Dickinson 356230) in collagen (Rat Tail Collagen, type I: Becton Dickinson 354236). Allow to gel for 1 hour at 37° C.

Inoculate the human vein endothelial cells (HUVEC ref: C-015-10C—cascade Biologics, INC) or porcine aortic endothelial cells (PAEC) at 15·10$^3$ cells/well in 400 µl of EBM medium (Clonetics C3121)+2% FBS+hEGF 10 µg/ml for the HUVECs and DMEM+3% FCS+2 mM glutamine+1 mM sodium pyruvate+1% nonessential amino acids (GIBCO) for the PAECs.

Stimulate with b-FGF (TEBU/Peprotech) 10 ng/ml or a-FGF (TEBU/Peprotech) 10 ng/ml in the presence or otherwise of the products of the invention for 24 h at 37° C. in the presence of 5% $CO_2$.

After 24 hours, fix the cells and stain the slide with the Masson trichrome before examination under the microscope X4 lens and image analysis (BIOCOM—Visiolab 2000 software).

For the test of angiogenesis in vitro induced by b-FGF or a-FGF, the compounds of the invention demonstrated a specific activity of between $10^{-7}$ M and $10^{-11}$ M.

Example 218

Model of Inflammatory Angiogenesis in Mice

Angiogenesis is required for the development of chronic inflammatory diseases such as rheumatoid arthritis, IBD, but also for the development of solid tumours. The formation of new vessels not only allows the perfusion of pathological tissues, but also the transport of cytokines responsible for establishing the chronicity of the disease.

The model described by Colville-Nash P. et al., (*D. JPET.*, 1995, Vol. 274 No. 3, pp. 1463-1472) makes it possible to study pharmacological agents capable of modulating the appearance of angiogenesis.

The animals, nonconsanguineous white mice of about 25 g, are anaesthetized with sodium pentobarbital (60 mg/kg; Sanofi Nutrition Santé Animale) by the intraperitoneal route.

An air pouch is created on the back of the mice by injecting 3 ml of air subcutaneously.

After becoming conscious, the animals receive a treatment, in general by force-feeding, and receive an injection of 0.5 ml of Freund's adjuvant (Sigma) with 0.1% croton oil (Sigma) in the pouch.

Seven days later, the mice are again anaesthetized and placed on a heating plate at 40° C. One ml of carmine red (5% in 10% gelatine—Aldrich Chemicals) is injected into the tail vein. The animals are then placed at 4° C. for 2-3 hours.

The skins are then removed and dried for 48 hours in an oven at 56° C. The dry tissues are weighed and placed in 1.8 ml of digestion buffer (2 mM dithiothreitol, 2 mM $Na_2HPO_4$, 1 mM EDTA, 12 U/ml papain) for 24 hours.

The stain is then dissolved in 0.2 ml of 5 M NaOH. The skins are centrifuged at 2000 g for 10 min. The supernatants are filtered on 0.2 µm cellulose acetate membranes. The filtrates are read in a spectrophotometer at 492 nm against a carmine red calibration series.

Two parameters are studied: the dry weight of the granuloma and the quantity of stain after digestion of this tissue.

The results are expressed as mean values (±SEM). The differences between the groups are tested with an ANOVA followed by Dunnet's test for which the reference group is the "solvent control" group.

The compounds of the invention are active by the oral route at doses of 0.1 to 100 mg/kg.

Example 219

Model of MATRIGEL Angiogenesis in Mice

The model described by Passaniti et al. (*Laboratory Investigation* (1992) 67 (4) pp. 519-524) makes it possible to study pharmacological agents capable of modulating the appearance of angiogenesis which is specifically induced by b-FGF. FGF2 (Peprotech) is added to Matrigel (Beckton Dickinson) kept in liquid form at 4° C., in an amount of 300 ng/ml. After homogenization, the mixture (0.5 ml) is subcutaneously injected into the base of the back of black female mice (C57/B16) of about 20 g, anaesthetized beforehand with sodium pentobarbital (60 mg/kg; Sanofi Nutrition Santé Animale) by the intraperitoneal route. The animals are treated by force-feeding. After 5 days, the mice are again anaesthetized and the skin of the base of the back is removed; at this stage, the qualitative differences in vascularization of the granuloma are evaluated (awarded scores) and the granulomas are photographed. An assay of DNA in the granulomas is then carried out in order to quantify its cellularity. For that, the isolated granulomas are digested with collagenase (3 mg/ml) overnight at 37° C. After centrifugation at 850 g for 10 min, the supernatant is discarded and the pellet is redissolved in 1.2 ml of PBS buffer containing 1 mM $CaCl_2$, 1 mM $MgCl_2$ and 5 mM glucose. The quantity of DNA present is measured with the aid of a kit (Cyquant-GR®, Molecular probe) according to the instructions of the supplier.

The results are expressed as mean values (±SEM). The differences between the groups are tested with an ANOVA followed by a Dunnet's test for which the reference group is the "solvent control" group.

For the histological studies, the granulomas are removed with the muscle and the skin, fixed overnight in a 10% formaldehyde solution and embedded in paraffin (Embedder Leica®). The granulomas are then sliced with the aid of a microtome (Leica) and stained with the Masson's trichrome stain. Neovascularization of the granulomas is then evaluated. The vascularization levels are between a value of 0 and 5.

The compounds of the invention are active by the oral route at doses of 0.1 to 100 mg/kg.

Example 220

Model of Tumour Angiogenesis in Mice

This model makes it possible to study pharmacological agents capable of modulating the appearance of angiogenesis specifically induced by tumour development. C56/B16 mice of about 20 g are anaesthetized with sodium pentobarbital (60 mg/kg; Sanofi Nutrition Santé Animale) by the intraperitoneal route. The tumours are established by subcutaneous injection on the back of mouse Lewis Lung cells in an amount of $2 \cdot 10^5$ cells/mouse. After 5 days, the mice are treated daily by force-feeding. The size of the tumours is measured twice per week for 21 days and the tumour volume is calculated using the formula: $[\pi/6(\omega)_1 \times \omega_2)]$, where $\omega_1$ represents the largest diameter and $\omega_2$ represents the smallest diameter.

The results are expressed as mean values (±SEM). The differences between the groups are tested with an ANOVA followed by a Dunnet's test for which the reference group is the "solvent control" group.

The compounds of the invention are active by the oral route at doses of 0.1 to 100 mg/kg.

The invention claimed is:
1. A compound of formula I,

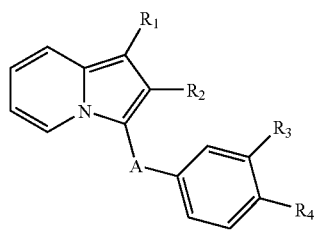

(I)

in which
$R_1$ represents a hydroxyl radical, a linear or branched alkoxy radical of 1 to 5 carbon atoms, a carboxyl radical, or a radical of formula:
—$NR_5R_6$
—NH—$SO_2$-Alk
—NH—$SO_2$-Ph
—NH—CO-Ph
—N(Alk)-CO-Ph
—NH—CO—NH-Ph
—NH—CO-Alk
—NH—$CO_2$-Alk
—O—$(CH_2)_n$-cAlk
—O-Alk-$COOR_7$
—O-Alk-O—$R_8$
—O-Alk-OH
—O-Alk-C($NH_2$):NOH
—O-Alk-$NR_5R_6$
—O-Alk-CN
—O—$(CH_2)_n$-Ph
—O-Alk-CO—$NR_5R_6$
—CO—NH—$(CH_2)_m$—$COOR_7$
—CO—NH-Alk
in which
Alk represents an alkyl radical or a linear or branched alkylene radical of 1 to 5 carbon atoms,
cAlk represents a cycloalkyl radical of 3 to 6 carbon atoms,
n represents an integer from 0 to 5,
m represents an integer from 1 to 5,
$R_5$ and $R_6$, which are identical or different, each represent a hydrogen atom, a linear or branched alkyl radical of 1 to 5 carbon atoms or a benzyl radical,
$R_7$ represents a hydrogen atom or an alkyl radical of 1 to 5 carbon atoms,
$R_8$ represents an alkyl radical of 1 to 5 carbon atoms or a radical —CO-Alk,
Ph represents a phenyl radical which is optionally substituted with one or more halogen atoms, with one or more alkoxy radicals of 1 to 5 carbon atoms, with one or more carboxyl radicals or with one or more alkoxycarbonyl radicals of 2 to 6 carbon atoms,
$R_2$ represents a hydrogen atom, an alkyl radical of 1 to 5 carbon atoms, a haloalkyl radical of 1 to 5 carbon atoms containing 3 to 5 halogen atoms, a cycloalkyl radical of 3 to 6 carbon atoms or a phenyl radical which is optionally substituted with one or more halogen atoms, with one or more alkoxy radicals of 1 to 5 carbon atoms, with one or more carboxyl radicals or with one or more alkoxycarbonyl radicals of 2 to 6 carbon atoms,
A represents a radical —CO—,
$R_3$ and $R_4$, which are identical or different, each represent an alkoxy radical of 1 to 5 carbon atoms, an amino radical, a carboxyl radical, an alkoxycarbonyl radical of 2 to 6 carbon atoms, a hydroxyl radical, a nitro radical, a hydroxyamino radical, a radical of formula
—Alk-$COOR_7$
—$NR_5R_6$
—NH-Alk-$COOR_7$
—NH—COO-Alk
—N($R_{11}$)—$SO_2$-Alk-$NR_9R_{10}$
—N($R_{11}$)—$SO_2$-Alk
—N($R_{11}$)-Alk-$NR_5R_6$
—N($R_{11}$)—CO-Alk-$NR_9R_{10}$
—N($R_{11}$)—CO-Alk
—N($R_{11}$)—CO—$CF_3$
—NH-Alk-HetN —O-Alk-CO—$NR_5R_6$
—O-Alk-HetN
in which n, m, Alk, $R_5$, $R_6$ and $R_7$ have the meaning given above for $R_1$, and
$R_9$ and $R_{10}$, which are identical or different, each represent a hydrogen atom or an alkyl radical of 1 to 5 carbon atoms,
$R_{11}$ represents a hydrogen atom or a radical -Alk-$COOR_{12}$ where $R_{12}$ represents a hydrogen atom, an alkyl radical of 1 to 5 carbon atoms or a benzyl radical,
HetN represents a 5- or 6-membered heterocycle containing at least one nitrogen atom and optionally another heteroatom chosen from nitrogen and oxygen,
or $R_3$ and $R_4$ form together a 5- to 6-membered unsaturated heterocycle, or a pharmaceutically acceptable salt thereof.

2. A compound according to claim 1, in which
$R_1$ represents a hydroxyl radical, a linear or branched alkoxy radical of 1 to 5 carbon atoms, a carboxyl radical, or a radical of formula:
—$NR_5R_6$
—NH—$SO_2$-Alk
—NH—$SO_2$-Ph
—NH—CO-Ph
—N(Alk)-CO-Ph
—NH—CO—NH-Ph
—NH—CO-Alk
—NH—$CO_2$-Alk
—O—$(CH_2)_n$-cAlk
—O-Alk-$COOR_7$
—O-Alk-O—$R_8$
—O-Alk-OH
—O-Alk-$NR_5R_6$
—O-Alk-CN
—O—$(CH_2)_n$-Ph
—O-Alk-CO—$NR_5R_6$
—CO—NH—$(CH_2)_m$—$COOR_7$
—CO—NH-Alk
in which
Alk represents an alkyl radical or a linear or branched alkylene radical of 1 to 5 carbon atoms,
cAlk represents a cycloalkyl radical of 3 to 6 carbon atoms,
n represents an integer from 0 to 5,
m represents an integer from 1 to 5,
$R_5$ and $R_6$, which are identical or different, each represent a hydrogen atom, a linear or branched alkyl radical of 1 to 5 carbon atoms or a benzyl radical,
$R_7$ represents a hydrogen atom or an alkyl radical of 1 to 5 carbon atoms,
$R_8$ represents an alkyl radical of 1 to 5 carbon atoms or a radical —CO-Alk,
Ph represents a phenyl radical which is optionally substituted with one or more halogen atoms, with one or more alkoxy radicals of 1 to 5 carbon atoms, with one or more carboxyl radicals or with one or more alkoxycarbonyl radicals of 2 to 6 carbon atoms,
$R_2$ represents an alkyl radical of 1 to 5 carbon atoms, a trifluoromethyl radical, a cycloalkyl radical of 3 to 6 carbon atoms or a phenyl radical which is optionally substituted with one or more halogen atoms, with one or more alkoxy radicals of 1 to 5 carbon atoms, with one or more carboxyl radicals or with one or more alkoxycarbonyl radicals of 2 to 6 carbon atoms,
A represents a radical —CO—,
$R_3$ and $R_4$, which are identical or different each represent an alkoxy radical of 1 to 5 carbon atoms, an amino radical, a carboxyl radical, an alkoxycarbonyl radical of 2 to 6 carbon atoms, a nitro radical, a hydroxyamino radical, a radical of formula
-Alk-$COOR_7$
—$NR_5R_6$
—NH-Alk-$COOR_7$
—NH—COO-Alk
—N($R_{11}$)—$SO_2$-Alk-$NR_9R_{10}$
—N($R_{11}$)—$SO_2$-Alk
—N($R_{11}$)-Alk-$NR_5R_6$
—N($R_{11}$)—CO-Alk-$NR_9R_{10}$
—N($R_{11}$)—CO-Alk
—N($R_{11}$)—CO—$CF_3$
—NH-Alk-HetN
in which n, m, Alk, $R_5$, $R_6$ and $R_7$ have the meaning given above for $R_1$, and
$R_9$ and $R_{10}$, which are identical or different, each represent a hydrogen atom or an alkyl radical of 1 to 5 carbon atoms,
$R_{11}$ represents a hydrogen atom or a radical -Alk-$COOR_{12}$ where $R_{12}$ represents a hydrogen atom, an alkyl radical of 1 to 5 carbon atoms or a benzyl radical,
HetN represents a 5- or 6-membered heterocycle containing at least one nitrogen atom and optionally another heteroatom chosen from nitrogen and oxygen.

3. A compound according to claim 2 wherein
$R_1$ represents an alkoxy radical of 1 to 5 carbon atoms, a carboxyl radical, a radical —O-Alk-COOH in which Alk represents an alkylene radical of 1 to 5 carbon atoms, a radical of formula —O-Alk-Ph in which Alk represents an alkylene radical of 1 to 5 carbon atoms and Ph represents a phenyl radical which is optionally substituted with one or more halogen atoms or with one or more alkoxy radicals of 1 to 5 carbon atoms or with one or more carboxyl radicals, a radical of formula —NH—CO-Ph, a radical of formula —NH—$SO_2$-Ph or a radical of formula —NH—CO—NH-Ph,
$R_2$ represents an alkyl radical of 1 to 5 carbon atoms,
A represents a radical —CO—, and
$R_3$ and $R_4$, which are different, each represent an alkoxy radical of 1 to 5 carbon atoms, an amino radical, a carboxyl radical or an alkoxycarbonyl radical of 2 to 6 carbon atoms.

4. A compound according to claim 1 selected from the group consisting of:
(4-amino-3-methoxyphenyl)(1-methoxy-2-methylindolizin-3-yl)methanone,
3-(4-amino-3-methoxybenzoyl)-2-methylindolizin-1-yl carboxylic acid,
2-{[3-(4-amino-3-methoxybenzoyl)-2-methylindolizin-1-yl]oxy}acetic acid,
(4-amino-3-methoxyphenyl){1-[(4-chlorobenzyl)oxy]-2-methylindolizin-3-yl}methanone,
(4-amino-3-methoxyphenyl){1-[(3-methoxybenzyl)oxy]-2-methylindolizin-3-yl}methanone,
4-({[3-(4-amino-3-methoxybenzoyl)-2-methylindolizin-1-yl]oxy}methyl)benzoic acid,
2-amino-5-[(1-methoxy-2-methylindolizin-3-yl)carbonyl]benzoic acid,
2-amino-5-({1-[(3-methoxybenzoyl)amino]-2-methylindolizin-3-yl}carbonyl)benzoic acid,
2-amino-5-({2-methyl-1-[(3,4,5-trimethoxybenzoyl)amino]indolizin-3-yl}carbonyl)benzoic acid, and
2-amino-5-({1-{[(3-methoxyphenyl)sulphonyl]amino}-2-methylindolizin-3-yl}carbonyl)benzoic acid
or a pharmaceutically acceptable salt thereof.

5. A method for preparing the compounds according to claim 1 wherein

A) an indolizine derivative of formula II,

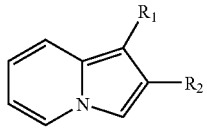

(II)

in which $R_1$ and $R_2$ have the meaning given for formula I, but $R_2$ does not represent a hydrogen atom or a haloalkyl radical, is condensed with a derivative of formula III,

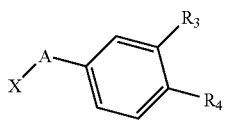

(III)

in which X represents a halogen atom and $R_3$ or $R_4$, which are identical or different, each represent a hydrogen atom, a nitro radical, a trifluoroacetamido radical or an alkoxycarbonyl radical of 2 to 6 carbon atoms, in order to obtain the compounds of formula Ia, Id or Ik,

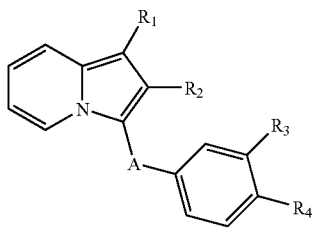

(Ia)

$R_3$ and/or $R_4$ = —$NO_2$

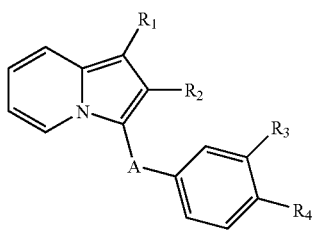

(Id)

$R_3$ and/or $R_4$ = —$CO_2$Alkyl

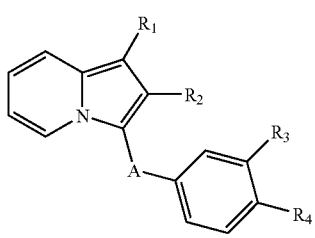

(Ik)

$R_3$ and/or $R_4$ = —NH—$COCF_3$ and then, a) the compounds of formula Ia are subjected to a reduction in order to obtain the compounds of formula Ib,

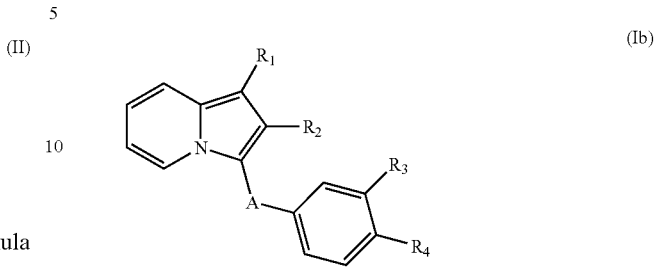

(Ib)

$R_3$ and/or $R_4$ = —$NH_2$ in which $R_3$ and/or $R_4$ represent an amino radical, which compounds of formula Ib then are subjected to the action of an alkyl halide in order to obtain the compounds of formula I in which $R_4$ and/or $R_3$ represent a radical —$NR_5R_6$ (in which $R_5$ represents a hydrogen atom and $R_6$ represents an alkyl radical of 1 to 5 carbon atoms) and a radical —NH-Alk-$NR_5R_6$ or a radical —NH-Alk-$COOR_7$ (in which $R_7$ does not represent a hydrogen atom) from which, by a subsequent saponification, the compounds of formula I are obtained in which $R_4$ and/or $R_3$ represent a radical —NH-Alk-$COOR_7$ in which $R_7$ represents a hydrogen atom, or are subjected to acylation in order to obtain the compounds of formula I in which $R_4$ and/or $R_3$ represent a radical —NH—CO-Alk, or a radical —NH—CO-Alk-$NR_9R_{10}$, which are then subjected to alkylation in order to obtain a radical —N($R_{11}$)—CO-Alk or a radical —N($R_{11}$)—CO-Alk-$NR_9R_{10}$ where $R_{11}$ represents a radical -Alk-$COOR_{12}$ in which $R_{12}$ does not represent a hydrogen atom, the latter compounds are then optionally subjected to saponification in order to obtain the compounds of formula I in which $R_4$ and/or $R_3$ represent a radical —N($R_{11}$)—CO-Alk or a radical —N($R_{11}$)—CO-Alk-$NR_9R_{10}$ where $R_{11}$ represents a radical -Alk-COOH, or are subjected to sulphonylation in order to obtain the compounds of formula I in which $R_4$ and/or $R_3$ represent a radical —NH—$SO_2$-Alk or a radical —NH—$SO_2$-Alk-$NR_9R_{10}$, which are then subjected to alkylation in order to obtain a radical —N($R_{11}$)—$SO_2$-Alk or a radical —N($R_{11}$)—$SO_2$-Alk-$NR_9R_{10}$ where $R_{11}$ represents a radical -Alk-$COOR_{12}$ in which $R_{12}$ does not represent a hydrogen atom, the latter compounds are then optionally subjected to saponification in order to obtain the compounds of formula I in which $R_4$ and/or $R_3$ represent a radical —N($R_{11}$)—$SO_2$-Alk or a radical —N($R_{11}$)—$SO_2$-Alk-$NR_9R_{10}$ where $R_{11}$ represents a radical -Alk-COOH b) the compounds of formula Id in which $R_3$ and/or $R_4$ represent an alkoxycarbonyl radical are subjected to saponification in order to obtain the compounds of formula I in which $R_3$ and/or $R_4$ represent a carboxyl radical, or c) when $R_1$ represents a benzyloxy radical, the compounds of formula Ia are subjected to the action of trifluoroacetic acid or the compounds of formula Id to hydrogenation, in order to obtain the compounds of formula If,

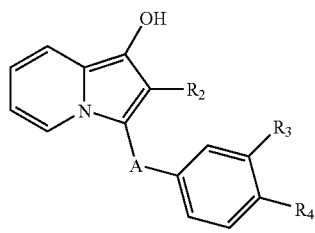
(If)

and then the compounds of formula If are subjected to O-alkylation in order to obtain the compounds of formula Ig,

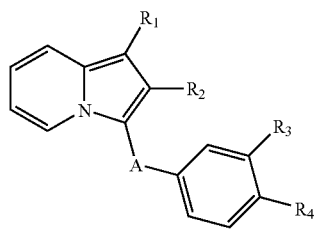
(Ig)

in which $R_3$ and/or $R_4$ have the meanings given above, and $R_1$ represents a linear or branched alkoxy radical of 1 to 5 carbon atoms, a radical —O—$(CH_2)_n$-cAlk, a radical —O-Alk-COOR$_7$, a radical —O-Alk-NR$_5$R$_6$, a radical —O—$(CH_2)_n$—Ph, or a radical —O-Alk-O—R$_8$— which, when R$_8$ represents a radical —COCH$_3$, can give, by subsequent saponification, a radical —O-Alk-OH—, or a radical —O-Alk-CN which, by treatment with hydroxylamine, gives a radical —O-Alk-C(NH$_2$)=NOH, or d) when $R_1$ represents an alkoxycarbonyl radical, the compounds of formula Ia are subjected to saponification in order to obtain the compounds of formula Ih,

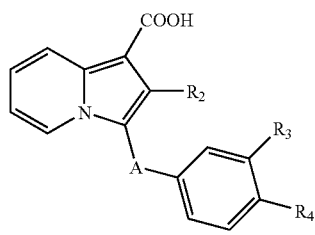
(Ih)

which are then subjected to the action of an amine derivative in order to obtain the compounds of formula I in which $R_1$ represents a radical —CO—NH-Alk, or to the action of an amino acid derivative in order to obtain the compounds of formula I in which $R_1$ represents a radical —CO—NH—$(CH_2)_m$—COOR$_7$ or e) when $R_1$ represents a radical —NH—CO$_2$tButyl, the compounds of formula Ia or Id are subjected
either to alkylation followed by deprotection and an optional second alkylation in order to obtain the compounds of formula Ii, or to deprotection, followed by acylation in order to obtain the compounds of formula Ij in which R$_5$ represents a hydrogen atom, followed by an optional alkylation in order to obtain the compounds of formula Ij in which R$_5$ represents an alkyl radical

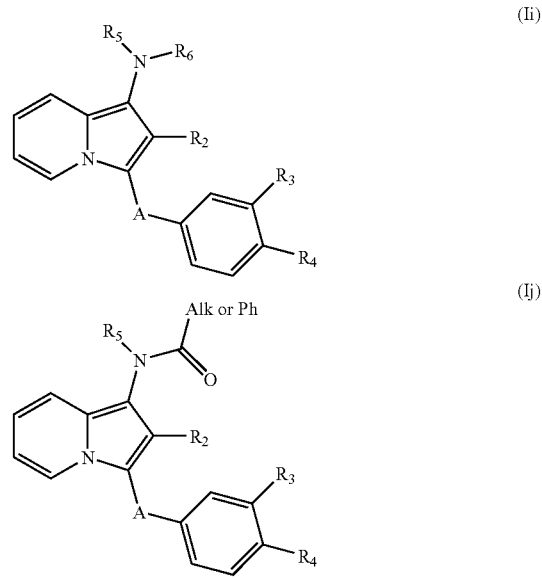
(Ii)

(Ij)

or f) when $R_1$ represents a radical —NH—CO$_2$tButyl, the compounds of formula Ik are subjected
either to deprotection, followed by acylation in order to obtain the compounds of formula Il

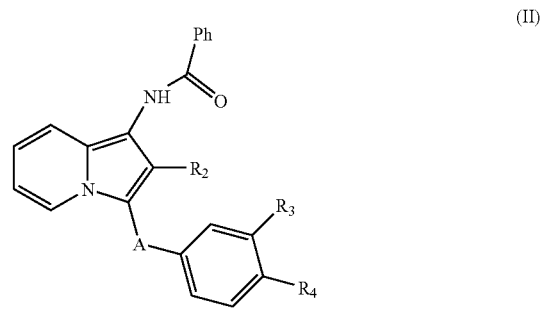
(Il)

or to deprotection followed by sulphonylation in order to obtain the compounds of formula Im

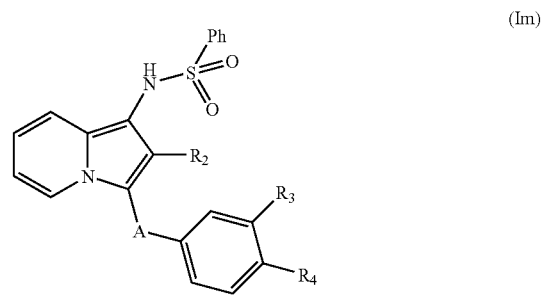
(Im)

or to deprotection, followed by a treatment with a phenyl isocyanate in order to obtain the compounds of formula In

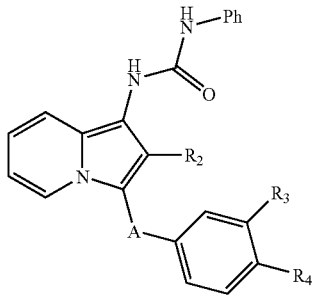
(In)

OR

B) when $R_1$ represents an electron-attracting group, $R_2$ represents a hydrogen atom or a haloalkyl radical and A represents a radical —CO—, pyridine is reacted with a bromoacetophenone of formula IV,

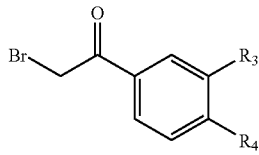
(IV)

in order to obtain the compounds of formula V,

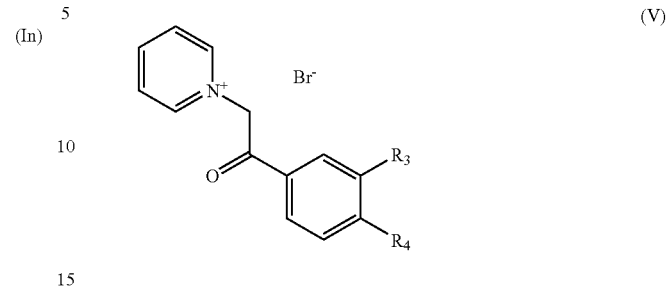
(V)

which are then subjected to a 1,3-dipolar cycloaddition with ethyl acrylate or a halogenated derivative of ethyl crotonate in the presence of an oxidizing agent in order to obtain the compounds of formula Ia in which $R_1$ represents an ethoxycarbonyl radical and $R_2$ represents a hydrogen atom or a haloalkyl radical.

6. A pharmaceutical composition comprising a therapeutically effective amount of a compound according to claim 1 together with a pharmaceutically acceptable excipient.

7. A pharmaceutical composition comprising a therapeutically effective amount of a compound according to claim 4 together with a pharmaceutically acceptable excipient.

* * * * *